United States Patent
Ogawa et al.

(10) Patent No.: US 8,609,753 B2
(45) Date of Patent: Dec. 17, 2013

(54) ACRYLIC RUBBER COMPOSITION AND CROSS-LINKED RUBBER PRODUCT

(75) Inventors: Tomonori Ogawa, Tokyo (JP); Masanobu Shinohara, Tokyo (JP); Tsutomu Yoshimura, Tokyo (JP); Kei Sakamoto, Tokyo (JP); Satoshi Kiriki, Tokyo (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 13/575,778

(22) PCT Filed: Jan. 28, 2011

(86) PCT No.: PCT/JP2011/051741
§ 371 (c)(1),
(2), (4) Date: Jul. 27, 2012

(87) PCT Pub. No.: WO2011/093444
PCT Pub. Date: Aug. 4, 2011

(65) Prior Publication Data
US 2012/0302674 A1    Nov. 29, 2012

(30) Foreign Application Priority Data

| Jan. 29, 2010 | (JP) | 2010-019346 |
| Mar. 30, 2010 | (JP) | 2010-076843 |
| Sep. 30, 2010 | (JP) | 2010-220695 |
| Sep. 30, 2010 | (JP) | 2010-220696 |
| Nov. 29, 2010 | (JP) | 2010-265633 |
| Nov. 29, 2010 | (JP) | 2010-265634 |
| Dec. 17, 2010 | (JP) | 2010-281975 |
| Dec. 17, 2010 | (JP) | 2010-281976 |

(51) Int. Cl.
*C08K 5/34* (2006.01)
*C08F 20/02* (2006.01)
*C08F 120/02* (2006.01)
*C08F 220/02* (2006.01)
*C08F 8/14* (2006.01)

(52) U.S. Cl.
USPC .......... 524/89; 524/83; 525/329.7; 525/330.1

(58) Field of Classification Search
USPC ........................................ 524/83
See application file for complete search history.

(56) References Cited

U.S. PATENT DOCUMENTS

| 2,983,731 | A | | 5/1961 | Meis |
| 3,489,749 | A | * | 1/1970 | Donald ............. 544/35 |
| 3,822,284 | A | * | 7/1974 | Werzner et al. ........ 548/440 |
| 4,343,921 | A | | 8/1982 | Piestert |
| 4,431,762 | A | | 2/1984 | Araki et al. |
| 6,093,853 | A | | 7/2000 | Nakagome et al. |
| 6,329,551 | B1 | | 12/2001 | Nakagome et al. |
| 2002/0016508 | A1 | | 2/2002 | Nakagome et al. |
| 2005/0159519 | A1 | | 7/2005 | Nakagome et al. |
| 2008/0071014 | A1 | * | 3/2008 | Ohishi et al. ............. 524/258 |

FOREIGN PATENT DOCUMENTS

| CZ | 221000 B1 | 4/1983 |
| EP | 0334500 A1 | 9/1989 |
| GB | 1347141 A | 2/1974 |
| JP | 55-69672 A | 2/1983 |
| JP | 58-17158 A | 2/1983 |
| JP | 4-174886 A | 6/1992 |
| JP | 09-053070 A | 2/1997 |
| JP | 10-298551 A | 11/1998 |
| JP | 11-21411 A | 1/1999 |
| JP | 2008-31330 A | 2/2008 |
| JP | 2008127518 A * | 6/2008 |
| JP | 2008-291083 A | 12/2008 |
| JP | 2009-7491 A | 1/2009 |
| JP | 2009-84514 A | 4/2009 |
| JP | 2010-174217 A | 8/2010 |
| JP | 2011-1428 A | 1/2011 |
| WO | WO 88/02007 | 3/1988 |
| WO | WO 02/081432 A2 | 10/2002 |
| WO | WO 2006/001299 A1 | 1/2006 |
| WO | WO 2007/020932 A1 | 2/2007 |

OTHER PUBLICATIONS

JP 2008-127518 A (2008), machine translation, JPO Advanced Industrial Property Network (AIPN).*
International Search Report issued in PCT/JP2011/051741, mailed on Apr. 26, 2011.
J. I. G. Cadogan et al.; Nitrene-induced Cyclisations Accompanied by Rearrangement in Thermolyses of . . . ; Journal of the Chemical Society; Perkin Transactions 1; No. 16; 1976; pp. 1749-1757.
Jan Bergman; Synthesis of Carbazoles Related to Carbazomycin, hyellezole and ellipticine; Tetrehedron; vol. 44; No. 16; pp. 5215-5228; 1988.
Nathan L. Smith; Cyanothylation of Some Carbasole Derivatives; Journal of the American Chemical Society; pp. 4313-4314; 1950; vol. 72 No. 9.
Official Action dated Jun. 18, 2013 issued in European Patent Application No. 11 737 153 4.
Sergio M. Bonesi et al.; A study of Substituent Effect on . . . ; Journal of Heterocyclic Chemistry; No. 2; pp. 161-171; 41; 161; 2004.
Shoji Matsumoto et al.; A Novel Reaction Promoted by Hydrogen Polyiodides . . . ; Chemistry Letters; vol. 2; 2002; pp. 134-135.

(Continued)

Primary Examiner — David W Wu
Assistant Examiner — Josephine Chang
(74) Attorney, Agent, or Firm — Birch, Stewart, Kolasch & Birch, LLP

(57) ABSTRACT

An acrylic rubber composition which contains, with respect to 100 parts by weight of acrylic rubber, a compound which is expressed by the following general formula (1) in 0.1 to 50 parts by weight and a cross-linking agent in 0.05 to 20 parts by weight is provided.

(1)

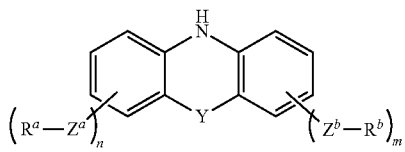

(where, in said general formula (1), Y indicates a chemical single bond or —$SO_2$—. $R^a$ and $R^b$ respectively independently indicate substitutable $C_1$ to $C_{30}$ organic groups. $Z^a$ and $Z^b$ respectively independently indicate chemical single bonds or —$SO_2$—. n and m respectively independently are 0 or 1, at least one of n and m being 1).

13 Claims, No Drawings

(56) References Cited

OTHER PUBLICATIONS

Ulf Pindur et al.; [4+2]cycloadditions of pyrano[3,4-b]indol-3-ones . . . ; Heterocycles; pp. 1751-1761; vol. 31; No. 10; 1990.

Madrid, et al. "Synthesis and Antitubercular Activity of Phenothiazines with Reduced Binding to Dopamine and Serotonin Receptors", Bioorganic & Medicinal Chemistry Letters 17(2007) 3014-3017.

Burmistrov et al., "New rearrangement of 10-arenesulfonylphenothiazines," Database Caplus [Online], Chemical Abstracts Service, Columbus, Ohio, US; 1976, XP-002711929.

Database Registry [Online], Chemical Abstracts Service, Columbus, Ohio, US; "10H-Phenothiazine, 2,8-diphenyl-" Sep. 24, 2007, XP-002711931.

Extended European Search Report for European Application No. 11737153.4, dated Sep. 12, 2013.

Extended European Search Report for European Application No. 11737154.2 dated Sep. 24, 2013.

Finzi, C, "Derivatives of thiophenylamine," Database Caplus [Online], Chemical Abstracts Service, Columbus, Ohio, US; 1932, XP-002711930.

Hallberg et al., "1,2-Didehydrophenothiazines: Preparation of 1-Alkyl and 1-Aryl-substituted Phenothiazines by Lithium-directed Alkylation" J. Chem. Soc. 1985, p. 969-971.

Katritzky et al, "Specific Synthesis of 1-Substituted Phenothiazines Using Carbon Dioxide Protection of the NH Group During Lithiation" Dept of Chem, Mar. 1988, p. 215-217.

Lafferty et al., "The Synthesis of Phenothiazines. VII. Methyl- and Arylsulfonylation of Phenothiazine and its 10-Substituted Derivatives," Smith Kline and French Labs. and Res. Inst. Temple University, vol. 27, Apr. 1962, pp. 1346-1351.

\* cited by examiner

ACRYLIC RUBBER COMPOSITION AND CROSS-LINKED RUBBER PRODUCT

TECHNICAL FIELD

The present invention relates to an acrylic rubber composition and cross-linked rubber product, more particularly relates to an acrylic rubber composition which gives a cross-linked rubber product which is superior in heat resistance and to a cross-linked rubber product obtained by cross-linking that acrylic rubber composition.

BACKGROUND ART

An acrylic rubber is superior in heat resistance, oil resistance, etc., so is being widely used in the automobile-related field etc. for hoses, seals, gaskets, and other rubber members.

On the other hand, such automobile-use rubber members, in particular, rubber members in the engine compartment, are being asked to provide further improved heat resistance performance due to the higher performance of turbo charger accompanying the higher output of engines and recent tougher exhaust gas regulations etc.

As a method for improving the heat resistance of rubber members, in the past, blending an antiaging agent into the acrylic rubber has been studied. As such an antiaging agent, diphenylamine-based antiaging agents etc. have been used. Among diphenylamine-based antiaging agents as well, 4,4'-bis($\alpha$,$\alpha$-dimethylbenzyl)diphenylamine is known to have a high heat resistance effect. However, the rubber which has blended 4,4'-bis($\alpha$,$\alpha$-dimethylbenzyl)diphenylamine which has been used in the past alone, cannot satisfy the recent demands for heat resistance. For this reason, various proposals are being made for further improving the heat resistance.

For example, Patent Document 1 discloses an acrylic rubber composition which is comprised of an acrylic rubber into which two types of diphenylamine-based antiaging agents are jointly blended. However, while the art which is described in Patent Document 1 improves the rate of change of tensile strength, rate of change of elongation, and rate of compression set in relatively short term heat resistance tests, the effect of improvement has been insufficient in high temperature, long term heat resistance tests.

Patent Document 2 discloses the art of using, as the antiaging agent which is blended into the acrylic rubber, instead of 4,4'-bis($\alpha$,$\alpha$-dimethylbenzyl)diphenylamine, a specific styrenated diphenylamine compound. Further, Patent Document 3 discloses an acrylic rubber composition which comprises a carboxyl group-containing acrylic rubber into which a secondary diamine-based antiaging agent and a secondary monoamine-based antiaging agent are jointly blended. However, while the arts which are described in Patent Document 2 and Patent Document 3 improve the rate of change of tensile strength in a relatively short term heat resistance test compared with using an antiaging agent constituted by 4,4'-bis($\alpha$, $\alpha$-dimethylbenzyl)diphenylamine alone, the effect of improvement of the rate of change of elongation or the rate of compression set was insufficient.

Furthermore, Patent Document 4 discloses a cross-linkable acrylic rubber composition which is comprised of acrylic rubber into which a polyvalent primary amine cross-linking agent and an antiaging agent constituted by p-amino diphenylamine are blended. The art which is described in Patent Document 4 improves the rate of change of elongation in a heat resistance test compared with the case of using an antiaging agent constituted by 4,4'-bis($\alpha$,$\alpha$-dimethylbenzyl) diphenylamine alone. However, to sufficiently meet the recent demands for heat resistance for acrylic rubber, further improvement has been desired.

PRIOR ART DOCUMENTS

Patent Documents
Patent Document 1: Japanese Patent Publication No. 11-21411
Patent Document 2: International Publication 2006/001299
Patent Document 3: Japanese Patent Publication No. 2009-7491
Patent Document 4: Japanese Patent Publication No. 2009-84514

SUMMARY OF THE INVENTION

Problem to be Solved by the Invention

The present invention has as its object the provision of an acrylic rubber composition which can give a cross-linked rubber product which is high in heat resistance, in particular which can suppress a drop in elongation and other physical properties even if exposed long term to high temperature conditions, and a cross-linked rubber product obtained by cross-linking the acrylic rubber composition.

Means for Solving the Problems

The inventors engaged in intensive research for achieving the above object and as a result discovered that by blending into acrylic rubber an antiaging agent constituted by a specific condensed heterocyclic compound and cross-linking agent in specific amounts, the object can be achieved and thereby completed the present invention.

That is, according to the present invention, there is provided an acrylic rubber composition which contains, with respect to 100 parts by weight of acrylic rubber, a compound which is expressed by the following general formula (1) in 0.1 to 50 parts by weight and a cross-linking agent in 0.05 to 20 parts by weight.

[Chemical Formula 1]

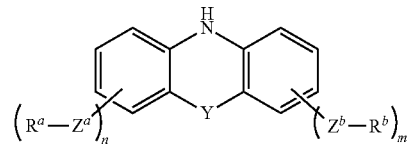

(1)

(where, in the general formula (1), Y indicates a chemical single bond or —$SO_2$—. $R^a$ and $R^b$ respectively independently indicate substitutable $C_1$ to $C_{30}$ organic groups. $Z^a$ and $Z^b$ respectively independently indicate chemical single bonds or —$SO_2$—. n and m respectively independently are 0 or 1, at least one of n and m being 1)

Preferably, in the compound which is expressed by the general formula (1), $R^a$ and $R^b$ respectively independently are substitutable linear or branched $C_2$ to $C_8$ alkyl groups or substitutable phenyl groups.

Preferably, in the compound which is expressed by the general formula (1), Y is —$SO_2$—, $R^a$ and $R^b$ respectively independently are substitutable linear or branched $C_2$ to $C_8$ alkyl groups, $Z^a$ and $Z^b$ are chemical single bonds, and n and m are 1.

Preferably, the content, with respect to 100 parts by weight of the acrylic rubber, of the compound which is expressed by the general formula (1) is 0.3 to 5 parts by weight.

Preferably, the acrylic rubber is a carboxyl group-containing acrylic rubber, epoxy group-containing acrylic rubber, halogen atom-containing acrylic rubber, or carboxyl group- and halogen atom-containing acrylic rubber.

Preferably, the acrylic rubber contains ethylene-acrylate rubber in 0.1 to 100 wt %.

Preferably, the acrylic rubber composition further contains at least one type of antiaging agent other than the compound which is expressed by the general formula (1), and the total content, with respect to 100 parts by weight of the acrylic rubber, of the compound which is expressed by the general formula (1) and the other antiaging agent is 0.1 to 50 parts by weight.

Further, according to the present invention, there is provided a cross-linked rubber product obtained by cross-linking any of the above described acrylic rubber compositions.

The cross-linked rubber product of the present invention is preferably an extruded product or a seal member.

Effects of the Invention

According to the present invention, it is possible to provide an acrylic rubber composition which can give a cross-linked rubber product which is high in heat resistance, in particular which can suppress a drop in elongation and other physical properties even if exposed long term to high temperature conditions, and a cross-linked rubber product obtained by cross-linking the acrylic rubber composition.

DESCRIPTION OF EMBODIMENTS

<Acrylic Rubber Composition>

The acrylic rubber composition of the present invention is a composition of an acrylic rubber which contains, with respect to the 100 parts of acrylic rubber, an antiaging agent constituted by a compound which is expressed by the later explained general formula (1) in 0.1 to 50 parts by weight and a cross-linking agent in 0.05 to 20 parts by weight.

<Acrylic Rubber>

The acrylic rubber which is used in the present invention need only be one which contains, in the molecule, a main ingredient (in the present application, meaning an ingredient which accounts for 50 wt. % or more of the total monomer units of the rubber) constituted by (meth)acrylic acid ester monomer [meaning an acrylic acid ester monomer and/or methacrylic acid ester monomer. Below, same for methyl (meth)acrylate etc.] units and is not particularly limited. For example, as the acrylic rubber which is used in the present invention, a polymer which contains, in the molecule, a main ingredient constituted by (meth)acrylic acid ester monomer units in 50 to 100 wt % and cross-linkable monomer units in 0 to 10 wt % etc. may be mentioned.

The (meth)acrylic acid ester monomer which forms the (meth)acrylic acid ester monomer units which are suitable as the main ingredient of the acrylic rubber which is used in the present invention is not particularly limited, but for example, a (meth)acrylic acid alkyl ester monomer, (meth)acrylic acid alkoxyalkyl ester monomer, etc. may be mentioned.

The (meth)acrylic acid alkyl ester monomer is not particularly limited, but esters of $C_1$ to $C_8$ alkanols and (meth)acrylic acid are preferable, specifically, methyl(meth)acrylate, ethyl (meth)acrylate, n-propyl (meth)acrylate, isopropyl(meth) acrylate, n-butyl(meth)acrylate, isobutyl(meth)acrylate, n-hexyl(meth)acrylate, 2-ethyl hexyl(meth)acrylate, cyclohexyl(meth)acrylate, etc. may be mentioned. Among these as well, ethyl(meth)acrylate and n-butyl(meth)acrylate are preferable, while ethyl acrylate and n-butyl acrylate are particularly preferable. These may be used as single type alone or as two or more types combined.

The (meth)acrylic acid alkoxyalkyl ester monomer is not particularly limited, but esters of $C_2$ to $C_8$ alkoxyalkyl alcohols and (meth)acrylic acid are preferable, specifically, methoxymethyl(meth)acrylate, ethoxymethyl(meth)acrylate, 2-methoxyethyl(meth)acrylate, 2-ethoxyethyl(meth)acrylate, 2-propoxyethyl(meth)acrylate, 2-butoxyethyl(meth) acrylate, 3-methoxypropyl(meth)acrylate, 4-methoxybutyl (meth)acrylate, etc. may be mentioned. Among these as well, 2-ethoxyethyl(meth)acrylate and 2-methoxyethyl(meth) acrylate are preferable, while 2-ethoxyethyl acrylate and 2-methoxyethyl acrylate are particularly preferable. These may be used as single type alone or as two or more types combined.

In the acrylic rubber which is used in the present invention, the content of the (meth)acrylic acid ester monomer units is 50 to 100 wt %, preferably 50 to 99.9 wt %, more preferably 60 to 99.5 wt %, furthermore preferably 70 to 99.5 wt %, particularly preferably 70 to 99 wt %. If the content of the (meth)acrylic acid ester monomer units is too small, the obtained cross-linked rubber product is liable to fall in weather resistance, heat resistance, and oil resistance.

Note that, in the present invention, the (meth)acrylic acid ester monomer units are preferably comprised of (meth) acrylic acid alkyl ester monomer units in 30 to 100 wt % and (meth)acrylic acid alkoxyalkyl ester monomer units in 70 to 0 wt %.

The cross-linkable monomer which forms the cross-linkable monomer units is not particularly limited, but, for example, α,β-ethylenically unsaturated carboxylic acid monomers; monomers which have epoxy groups; monomers which have halogen atoms; diene monomers; etc. may be mentioned.

The α,β-ethylenically unsaturated carboxylic acid monomer is not particularly limited, but, for example, $C_3$ to $C_{12}$ α,β-ethylenically unsaturated monocarboxylic acids, $C_4$ to $C_{12}$ α,β-ethylenically unsaturated dicarboxylic acids, monoesters of $C_4$ to $C_{12}$ α,β-ethylenically unsaturated dicarboxylic acids and $C_1$ to $C_8$ alkanols, etc. may be mentioned.

As specific examples of a $C_3$ to $C_{12}$ α,β-ethylenically unsaturated monocarboxylic acid, acrylic acid, methacrylic acid, α-ethyl acrylic acid, crotonic acid, cinnamic acid, etc. may be mentioned.

As specific examples of a $C_4$ to $C_{12}$ α,β-ethylenically unsaturated dicarboxylic acid, butene dioic acid such as fumaric acid, and maleic acid; itaconic acid; citraconic acid; chloromaleic acid; etc. may be mentioned.

As specific examples of a monoester of $C_4$ to $C_{12}$ α,β-ethylenically unsaturated dicarboxylic acids and $C_1$ to $C_8$ alkanols, butene dioic acid mono chain-like alkyl ester such as monomethyl fumarate, monoethyl fumarate, mono n-butyl fumarate, monomethyl maleate, monoethyl maleate, and mono n-butyl maleate; butene dioic acid monoester which has an alicyclic structure such as monocyclopentyl fumarate, monocyclohexyl fumarate, monocyclohexenyl fumarate, monocyclopentyl maleate, monocyclohexyl maleate, and monocyclohexenyl maleate; itaconate monoester such as monomethyl itaconate, monoethyl itaconate, mono n-butyl itaconate, and monocyclohexyl itaconate; etc. may be mentioned.

Among these as well, butene dioic acid mono chain-like alkyl ester or butene dioic acid monoester which has an alicyclic structure are preferable, mono n-butyl fumarate, mono n-butyl maleate, monocyclohexyl fumarate, and monocyclohexyl maleate are more preferable, and mono n-butyl fumarate is furthermore preferable. These α,β-ethylenically unsaturated carboxylic acid monomers may be used as single type alone or as two or more types combined. Note that, among the monomers, dicarboxylic acids include ones present as anhydrides.

In the present invention, when using, as a cross-linkable monomer, an α,β-ethylenically unsaturated carboxylic acid monomer, the acrylic rubber can be made a carboxyl group-containing acrylic rubber. If making the acrylic rubber a carboxyl group-containing acrylic rubber, the heat aging resistance of the acrylic rubber can be improved.

When the acrylic rubber which is used in the present invention is a carboxyl group-containing acrylic rubber, the content of the α,β-ethylenically unsaturated carboxylic acid monomer units is preferably 0.1 to 10 wt %, more preferably 0.5 to 7 wt %, furthermore preferably 1 to 5 wt %. If the content of the α,β-ethylenically unsaturated carboxylic acid monomer units is too small, the cross-linking becomes insufficient and the obtained cross-linked rubber product becomes poor in shape retention in some cases. On the other hand, if the content of the α,β-ethylenically unsaturated carboxylic acid monomer units is too great, the obtained cross-linked rubber product may fall in elongation or increase in rate of compression set.

Further, when the acrylic rubber which is used in the present invention is a carboxyl group-containing acrylic rubber, the content of the carboxyl groups, that is, the number of moles of the carboxyl groups per acrylic rubber 100 g (ephr), is preferably $4 \times 10^{-4}$ to $4 \times 10^{-1}$ (ephr), more preferably $1 \times 10^{-3}$ to $2 \times 10^{-1}$ (ephr), furthermore preferably $5 \times 10^{-3}$ to $1 \times 10^{-1}$ (ephr). If the content of the carboxyl groups is too small, the cross-linking becomes insufficient, the obtained cross-linked rubber product becomes insufficient in mechanical properties, and the surface skin of the molded product is liable to lack smoothness. On the other hand, if too great, the obtained cross-linked rubber product may fall in elongation or increase in rate of compression set.

The monomer which has epoxy groups is not particularly limited, but for example, epoxy group-containing (meth)acrylic acid esters, epoxy group-containing ethers, etc. may be mentioned.

As specific examples of an epoxy group-containing (meth) acrylic acid ester, glycidyl(meth)acrylate etc. may be mentioned.

As specific examples of a epoxy group-containing ether, allylglycidyl ether, vinylglycidyl ether, etc. may be mentioned. Among these as well, glycidyl methacrylate and allylglycidyl ether are preferable. These monomers which have epoxy groups can be used as single type alone or as two or more types combined.

In the present invention, when using as the cross-linkable monomer the monomers which have epoxy groups, the acrylic rubber can be made an epoxy group-containing acrylic rubber.

When the acrylic rubber which is used in the present invention is an epoxy group-containing acrylic rubber, the content of the monomer units which have epoxy groups is preferably 0.1 to 10 wt %, more preferably 0.5 to 7 wt %, furthermore preferably 0.5 to 5 wt %. If the content of the monomer units which have epoxy groups is too small, the cross-linking becomes insufficient and the obtained cross-linked rubber product becomes poor in shape retention in some cases, while if the content of the monomer units which have epoxy groups is too great, the obtained cross-linked rubber product may fall in elongation or increase in the rate of compression set.

The monomer which has halogen atoms is not particularly limited, but for example, unsaturated alcohol esters of halogen-containing saturated carboxylic acids, (meth)acrylic acid haloalkyl esters, (meth)acrylic acid haloacyloxyalkyl esters, (meth)acrylic acid (haloacetylcarbamoyloxy)alkyl esters, halogen-containing unsaturated ethers, halogen-containing unsaturated ketones, halomethyl group-containing aromatic vinyl compounds, halogen-containing unsaturated amides, haloacetyl group-containing unsaturated monomers, etc. may be mentioned.

As specific examples of an unsaturated alcohol ester of halogen-containing saturated carboxylic acids, vinyl chloroacetate, vinyl 2-chloropropionate, allyl chloroacetate, etc. may be mentioned.

As specific examples of a (meth)acrylic acid haloalkyl ester, chloromethyl(meth)acrylate, 1-chloroethyl(meth)acrylate, 2-chloroethyl(meth)acrylate, 1,2-dichloroethyl(meth) acrylate, 2-chloropropyl(meth)acrylate, 3-chloropropyl (meth)acrylate, 2,3-dichloropropyl(meth)acrylate, etc. may be mentioned.

As specific examples of a (meth)acrylic acid haloacyloxyalkyl ester, 2-(chloroacetoxy)ethyl(meth)acrylate, 2-(chloroacetoxy)propyl(meth)acrylate, 3-(chloroacetoxy)propyl (meth)acrylate, 3-(hydroxycycloacetoxy)propyl(meth) acrylate, etc. may be mentioned.

As specific examples of a (meth)acrylic acid (haloacetylcarbamoyloxy)alkyl ester, 2-(chloroacetylcarbamoyloxy) ethyl(meth)acrylate, 3-(chloroacetylcarbamoyloxy)propyl (meth)acrylate, etc. may be mentioned.

As specific examples of a halogen-containing unsaturated ether, chloromethylvinyl ether, 2-chloroethyl vinyl ether, 3-chloropropylvinyl ether, 2-chloroethylallyl ether, 3-chloropropylallyl ether, etc. may be mentioned.

As specific examples of a halogen-containing unsaturated ketone, 2-chloroethylvinyl ketone, 3-chloropropylvinyl ketone, 2-chloroethylallyl ketone, etc. may be mentioned.

As specific examples of a halomethyl group-containing aromatic vinyl compound, p-chloromethyl styrene, m-chloromethylstyrene, o-chloromethylstyrene, p-chloromethyl-α-methylstyrene, etc. may be mentioned.

As specific examples of a halogen-containing unsaturated amide, N-chloromethyl(meth)acrylamide etc. may be mentioned.

As specific examples of a haloacetyl group-containing unsaturated monomer, 3-(hydroxycycloacetoxy)propylallyl ether, p-vinyl benzylchloroacetic acid ester, etc. may be mentioned.

Among these as well, unsaturated alcohol esters of halogen-containing saturated carboxylic acids and halogen-containing unsaturated ethers are preferable, vinyl chloroacetate and 2-chloroethylvinyl ether are more preferable, and vinyl chloroacetate is further preferable. These monomers which have halogen atoms may be used as single type alone or as two or more types combined.

In the present invention, when using a monomer which has halogen atoms as a cross-linkable monomer, the acrylic rubber can be made a halogen atom-containing acrylic rubber.

When the acrylic rubber which is used in the present invention is a halogen atom-containing acrylic rubber, the content of the monomer units which have halogen atoms is preferably 0.1 to 10 wt %, more preferably 0.5 to 7 wt %, furthermore preferably 0.5 to 5 wt %. If the content of the monomer units which have halogen atoms is too small, the cross-linking becomes insufficient and the obtained cross-linked rubber product becomes poor in shape retention in some cases. On the other hand, if the content of the monomer units which have halogen atoms is too large, the obtained cross-linked rubber product may fall in elongation or increase in the rate of compression set.

Further, in the present invention, by using, as the cross-linkable monomers, an α,β-ethylenically unsaturated carboxylic acid monomer and a monomer which has halogen atoms, the acrylic rubber can be made a carboxyl group- and halogen atom-containing acrylic rubber.

When the acrylic rubber which is used in the present invention is a carboxyl group- and halogen atom-containing acrylic rubber, as specific examples of a cross-linkable monomer, ones similar to the above-mentioned carboxyl group-containing acrylic rubber and halogen atom-containing acrylic rubber may be mentioned. Among these as well, joint use of methacrylic acid and p-chloromethylstyrene is preferable.

When the acrylic rubber which is used in the present invention is a carboxyl group- and halogen atom-containing acrylic rubber, the total content of the α,β-ethylenically unsaturated carboxylic acid monomer units and monomer units which have halogen atoms is preferably 0.1 to 10 wt %, more preferably 0.5 to 7 wt %, furthermore preferably 0.5 to 5 wt %. If the content of these α,β-ethylenically unsaturated carboxylic acid monomer units and monomer units which have halogen atoms is too small, the cross-linking becomes insufficient and the obtained cross-linked rubber product becomes poor in shape retention in some cases. On the other hand, if the total content of the α,β-ethylenically unsaturated carboxylic acid monomer units and monomer units which have halogen atoms is too large, the obtained cross-linked rubber product may fall in elongation or increase in the rate of compression set.

As the ratio of contents of the α,β-ethylenically unsaturated carboxylic acid monomer units and the monomer units which have halogen atoms, a weight ratio of [α,β-ethylenically unsaturated carboxylic acid monomer units:monomer units which have halogen atoms] of [1:1.5 to 1:10] is preferable, and [1:2 to 1:8] is more preferable.

As the diene monomer, a conjugated diene monomer or non-conjugated diene monomer may be mentioned.

As specific examples of a conjugated diene monomer, 1,3-butadiene, isoprene, piperylene, etc. may be mentioned.

As specific examples of a non-conjugated diene monomer, ethylidene norbornene, dicyclopentadiene, dicyclopentadienyl(meth)acrylate, 2-dicyclopentadienylethyl(meth)acrylate, etc. may be mentioned.

Note that, when the acrylic rubber which is used in the present invention is the above-mentioned carboxyl group-containing acrylic rubber, epoxy group-containing acrylic rubber, halogen atom-containing acrylic rubber, or carboxyl group- and halogen atom-containing acrylic rubber, in accordance with need, other cross-linkable monomer units may also be included. The cross-linkable monomers which form the other cross-linkable monomer units may be used as single type alone or as two or more types combined. In the acrylic rubber which is used in the present invention, the content of the other cross-linkable monomer units is preferably 0 to 9.9 wt %, more preferably 0 to 6.5 wt %, furthermore preferably 0 to 4.5 wt %, particularly preferably 0 to 4 wt %. (Provided, however, that, in the acrylic rubber, the total amount of all of the cross-linkable monomer units is preferably 0.1 to 10 wt %, more preferably 0.5 to 7 wt %, furthermore preferably 0.5 to 5 wt %, particularly preferably 1 to 5 wt %.) If the content of these cross-linkable monomer units is too great, the obtained cross-linked rubber product may fall in elongation or increase in the rate of compression set.

Further, the acrylic rubber which is used in the present invention may have, in addition to the (meth)acrylic acid ester monomer units and cross-linkable monomer units, in accordance with need, a (meth)acrylic acid ester monomer and units of other monomer which can copolymerize with the cross-linkable monomer.

The copolymerizable other monomer is not particularly limited, but, for example, aromatic vinyl monomers, α,β-ethylenically unsaturated nitrile monomers, monomers which have two or more acryloyloxy groups (hereinafter sometimes referred to as "polyfunctional acryl monomers"), olefin-based monomers, vinyl ether compounds, etc. may be mentioned.

As specific examples of an aromatic vinyl monomer, styrene, α-methylstyrene, divinyl benzene, etc. may be mentioned.

As specific examples of an α,β-ethylenically unsaturated nitrile monomer, acrylonitrile, methacrylonitrile, etc. may be mentioned.

As specific examples of a polyfunctional acryl monomer, ethyleneglycol di(meth)acrylate, propyleneglycol di(meth)acrylate, etc. may be mentioned.

As specific examples of an olefin-based monomer, ethylene, propylene, 1-butene, 1-octene, etc. may be mentioned.

As specific examples of a vinyl ether compound, vinyl acetate, ethyl vinyl ether, n-butylvinyl ether. etc. may be mentioned.

Among these as well, styrene, acrylonitrile, methacrylonitrile, ethylene, and vinyl acetate are preferable, and acrylonitrile, methacrylonitrile, ethylene, and vinyl acetate are more preferable.

The copolymerizable other monomers may be used as single type alone or two or more types combined. In the acrylic rubber which is used in the present invention, the content of the units of the other monomer is 0 to 50 wt %, preferably 0 to 49.9 wt %, more preferably 0 to 39.5 wt %, furthermore preferably 0 to 29.5 wt %, particularly preferably 0 to 29 wt %.

The acrylic rubber which is used in the present invention can be obtained by polymerizing the above monomers. As the type of the polymerization reaction, any of the emulsion polymerization method, suspension polymerization method, bulk polymerization method, and solution polymerization method can be used, but from the viewpoint of the ease of control of the polymerization reaction etc., use of the emulsion polymerization method under ordinary pressure, which is generally used as the method of production of conventional known acrylic rubber, is preferable.

The emulsion polymerization may be either of the batch type, semi batch type, or continuous type. The polymerization is usually performed at 0 to 70° C., preferably 5 to 50° C. in temperature range.

The thus produced acrylic rubber which is used in the present invention has a Mooney viscosity ($ML_{1+4}$, 100° C.) (Polymer Mooney) of preferably 10 to 80, more preferably 20 to 70, furthermore preferably 25 to 60.

In the present invention, the thus produced acrylic rubber can be used as single type alone or as two or more types combined.

In the present invention, as the thus produced acrylic rubber, one which contains ethylene-acrylate rubber in 0.1 to 100 wt. % may be used.

When using as the acrylic rubber one which contains ethylene-acrylate rubber in 0.1 to 100 wt %, the ratio of the ethylene-acrylate rubber and the acrylic rubber other than the ethylene-acrylate rubber is usually "ethylene-acrylate rubber:acrylic rubber other than ethylene-acrylate rubber"=0.1 to 100 wt %:99.9 to 0 wt %, preferably 10 to 100 wt %:90 to 0 wt %, more preferably 20 to 100 wt %:80 to 0 wt %. If the ratio of the ethylene-acrylate rubber is within that range, it is possible to make the workability of the acrylic rubber and the strength and other mechanical properties and heat resistance of the obtained cross-linked rubber product excellent.

As the ethylene-acrylate rubber, a polymer which contains, in its molecule, a main ingredient constituted by (meth) acrylic acid ester monomer units in 50 to 99.9 wt %, ethylene monomer units in 0.1 to 50 wt %, and cross-linkable monomer units in 0 to 10 wt % is preferable.

Further, as an acrylic rubber other than ethylene-acrylate rubber, a polymer which contains the above-mentioned main ingredient constituted by (meth)acrylic acid ester monomer units in 50 to 100 wt % and cross-linkable monomer units in 0 to 10 wt % etc. may be used.

The (meth)acrylic acid ester monomer which forms the (meth)acrylic acid ester monomer units which are suitable as the main ingredient of the ethylene-acrylate rubber is not particularly limited, but the above-mentioned (meth)acrylic acid alkyl ester monomer, a (meth)acrylic acid alkoxyalkyl ester monomer, etc. may be mentioned.

In the ethylene-acrylate rubber, the content of the (meth) acrylic acid ester monomer units is preferably 50 to 99.9 wt %, more preferably 59.5 to 99 wt %, furthermore preferably 69 to 98 wt %. If the content of the (meth)acrylic acid ester monomer units is too small, the obtained cross-linked rubber product is liable to fall in weather resistance, heat resistance, and oil resistance.

Note that, in the ethylene-acrylate rubber, the (meth) acrylic acid ester monomer units are preferably comprised of (meth)acrylic acid alkyl ester monomer units in 30 to 100 wt % and (meth)acrylic acid alkoxyalkyl ester monomer units in 70 to 0 wt %.

The ethylene-acrylate rubber which is used in the present invention has ethylene monomer units as an essential ingredient. The content of the ethylene monomer units is preferably 0.1 to 50 wt %, more preferably 0.5 to 40 wt %, furthermore preferably 1 to 30 wt %. If the content of the ethylene monomer units is within the above range, the obtained cross-linked rubber product is excellent in strength and other mechanical properties, weather resistance, heat resistance, and oil resistance.

The ethylene-acrylate rubber may contain, in addition to the (meth)acrylic acid ester monomer units and ethylene monomer units, cross-linkable monomer units. Note that, as the cross-linkable monomer units, the ones mentioned above may be mentioned. In the ethylene-acrylate rubber, the content of the cross-linkable monomer units is preferably 0 to 10 wt %, more preferably 0.5 to 7 wt %, furthermore preferably 1 to 5 wt %. If the content of the cross-linkable monomer units is too large, the obtained cross-linked rubber product may fall in elongation or increase in the rate of compression set.

Note that, among the above-mentioned cross-linkable monomers as well, as the cross-linkable monomer which forms parts of the monomer units of the ethylene-acrylate rubber and acrylic rubber other than the ethylene-acrylate rubber, use of an α,β-ethylenically unsaturated carboxylic acid monomer is preferable. Because the ethylene-acrylate rubber which is used in the present invention can be made a carboxyl group-containing ethylene-acrylate rubber which has carboxyl groups as cross-linking points, due to this, the acrylic rubber which is used in the present invention can be improved in heat aging resistance.

Further, the ethylene-acrylate rubber which is used in the present invention may have, in addition to (meth)acrylic acid ester monomer units, ethylene monomer units, and cross-linkable monomer units, in accordance with need, units of other monomers which are copolymerizable with (meth) acrylic acid ester monomers, ethylene, and cross-linkable monomers. As the copolymerizable other monomers, the above-mentioned ones may be mentioned. In the ethylene-acrylic rubber which is used in the present invention, the content of the units of the other monomers is preferably 0 to 49.9 wt %, more preferably 0 to 39.5 wt %, furthermore preferably 0 to 29 wt %.

The ethylene-acrylate rubber which forms the acrylic rubber which is used in the present invention can be obtained by polymerization of the above monomers. As the type of the polymerization reaction, as explained above, any of the emulsion polymerization method, suspension polymerization method, bulk polymerization method, and solution polymerization method can be used. Any polymerization method can be selected.

When the acrylic rubber which is used in the present invention contains ethylene-acrylate rubber and an acrylic rubber other than the ethylene-acrylate rubber, the ethylene-acrylate rubber which is obtained by the above-mentioned methods and the acrylic rubber other than the ethylene-acrylate rubber can be mixed by a known method to obtain the acrylic rubber which is used in the present invention. The method of mixing is not particularly limited, but the method of isolating the respective acrylic rubbers, then dry blending them is suitable.

<Antiaging Agent>

The antiaging agent which is used in the present invention is a compound which is expressed by the following general formula (1).

[Chemical Formula 2]

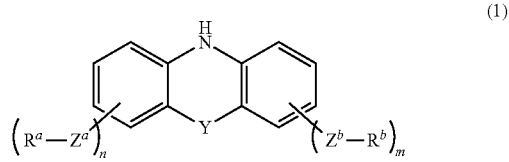

(1)

(where, in the general formula (1), Y indicates a chemical single bond or $-SO_2-$. $R^a$ and $R^b$ respectively independently indicate substitutable $C_1$ to $C_{30}$ organic groups. $Z^a$ and $Z^b$ respectively independently indicate chemical single bonds or $-SO_2-$. n and m respectively independently are 0 or 1, at least one of n and m being 1).

In the general formula (1), Y is a chemical single bond or $-SO_2-$, while $-SO_2-$ is preferable.

In the general formula (1), $R^a$ and $R^b$ respectively independently indicate substitutable $C_1$ to $C_{30}$ organic groups.

The $C_1$ to $C_{30}$ organic group which constitute the $R^a$ and $R^b$ are not particularly limited, but for example, $C_1$ to $C_{30}$ alkyl group such as methyl group, ethyl group, n-propyl group, isopropyl group, n-butyl group, isobutyl group, sec-butyl group, t-butyl group, n-pentyl group, n-hexyl group, n-heptyl group, n-octyl group, n-nonyl group, and n-decyl group; $C_3$ to $C_{30}$ cycloalkyl group such as cyclopropyl group, cyclopentyl group, cyclohexyl group, cycloheptyl group, and cyclooctyl group; $C_6$ to $C_{30}$ aryl group such as phenyl group, biphenyl group, naphthyl group, and anthranyl group; $C_1$ to $C_{30}$ alkoxy group such as methoxy group, ethoxy group, n-propoxy group, isopropoxy group, n-butoxy group, isobutoxy group, sec-butoxy group, t-butoxy group, n-pentyloxy group, and n-hexyloxy group; etc. may be mentioned.

Further, the above-mentioned organic groups which constitute $R^a$ and $R^b$ may also have a substituent. As the position of the substituent, any position may be used.

As such a substituent, when the organic group is an alkyl group, halogen atom such as fluorine atom, chlorine atom, and bromine atom; $C_1$ to $C_{10}$ alkoxy group such as methoxy group, ethoxy group, and isopropoxy group; nitro group; cyano group; substitutable phenyl group such as phenyl group, 4-methylphenyl group, and 2-chlorophenyl group; etc. may be mentioned.

Further, when the organic group is a cycloalkyl group or aryl group, as the substituent, halogen atom such as fluorine atom, chlorine atom, and bromine atom; $C_1$ to $C_{10}$ alkoxy group such as methoxy group, ethoxy group, and isopropoxy group; nitro group; cyano group; $C_1$ to $C_{10}$ alkyl group such as methyl group, ethyl group, and t-butyl group; etc. may be mentioned.

Furthermore, when the organic group is an alkoxy group, as the substituent, halogen atom such as fluorine atom, chlorine atom, and bromine atom; nitro group; cyano group; etc. may be mentioned.

Note that, in the present invention, when the organic groups which constitute the $R^a$ and $R^b$ have substituents, the numbers of carbon atoms of the organic groups do not include the numbers of carbon atoms of the substituents. That is, the organic groups which constitute the $R^a$ and $R^b$ should have numbers of carbon atoms, minus the numbers of atoms which are included in the substituents, of 1 to 30 in range. For example, when the organic groups which constitute the $R^a$ and $R^b$ are methoxyethyl groups, the numbers of carbon atoms of the organic groups become 2. That is, in this case, since the methoxy group is a substituent, so the numbers of carbon atoms of the organic groups become the numbers of carbon atoms minus those of methoxy group as the substituent.

In the present invention, as $R^a$ and $R^b$, respectively independently, substitutable $C_2$ to $C_{20}$ alkyl groups or substitutable $C_6$ to $C_{30}$ aryl groups are preferable, substitutable linear or branched $C_2$ to $C_{20}$ alkyl groups or substitutable phenyl groups or substitutable naphthyl groups are more preferable, substitutable linear or branched $C_2$ to $C_8$ alkyl groups or substitutable phenyl groups are furthermore preferable, and substitutable linear or branched $C_2$ to $C_8$ alkyl groups are particularly preferable.

As preferable specific examples of the organic groups which constitute such $R^a$ and $R^b$, an α-methylbenzyl group, α,α-dimethylbenzyl group, t-butyl group, phenyl group, 4-methylphenyl group, etc. may be mentioned. Among these as well, an α,α-dimethylbenzyl group or 4-methylphenyl group is more preferable, while an α,α-dimethylbenzyl group is furthermore preferable. Note that, these may be set respectively independently.

Further, in the general formula (1), $Z^a$ and $Z^b$ are respectively independently chemical single bonds or —$SO_2$—. Chemical single bonds are preferable.

Furthermore, in the general formula (1), n and m are respectively independently 0 or 1, and at least one of n and m is 1. Note that, n and m are preferably both 1.

In the present invention, as the compound which is expressed by the general formula (1), any of the compounds which are expressed by the following general formulas (2) to (8) is preferable.

[Chemical Formula 3]

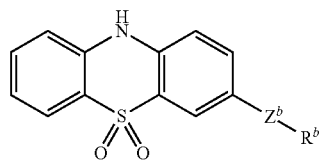

(2)

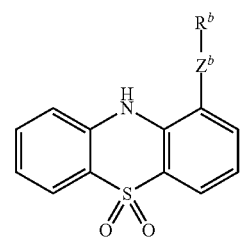

(3)

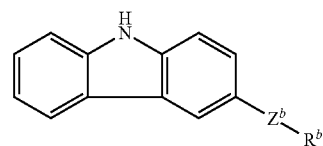

(4)

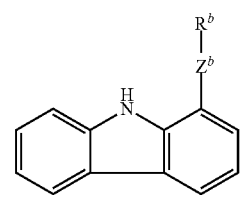

(5)

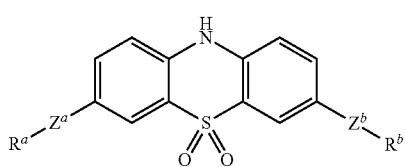

(6)

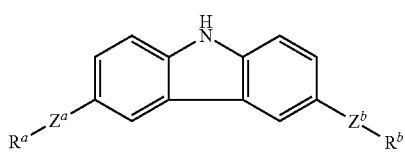

(7)

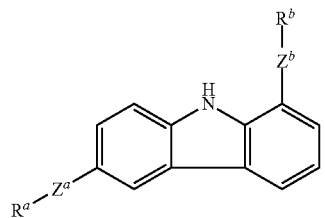

(8)

(wherein, in the general formulae (2) to (8), $R^a$, $R^b$, $Z^a$, and $Z^b$ are similar to the general formula (1)).

Among the compounds which are expressed by the general formulae (2) to (8) as well, compounds which are expressed by the general formulae (2), (6), and (7) are preferable, while a compound which is expressed by the general formula (6) is more preferable.

Further, among the general formulae (2) to (8), —$Z^a$—$R^a$ and —$Z^b$—$R^b$ respectively independently are preferably α-methylbenzyl groups, α,α-dimethylbenzyl groups, t-butyl groups, phenylsulfonyl groups, or 4-methylphenylsulfonyl groups, more preferably α,α-dimethylbenzyl groups or 4-methylphenylsulfonyl groups, furthermore preferably α,α-dimethylbenzyl groups.

That is, in the present invention, in the general formula (1), it is preferable that Y is —SO$_2$—, R$^a$ and R$^b$ are respectively independently substitutable linear or branched C$_2$ to C$_8$ alkyl groups, Z$^a$ and Z$^b$ are chemical single bonds, and n and m are 1.

Next, the method of production of the compound which is expressed by the general formula (1) will be explained.

When the compound which is expressed by the general formula (1) is a compound wherein Y is —SO$_2$—, it is possible to apply the method of production of known phenothiazine-based compounds to obtain a compound of the general formula (1) where Y is S, then oxidizing the obtained compound.

Further, the compound which is expressed by the general formula (1) can be obtained by using a compound which is expressed by the following general formula (9) [phenothiazine (Y$^1$=S) or carbazole (Y$^1$=chemical single bond)] as a starting material and using a known reaction method to introduce substituents (—Z$^a$—R$^a$, —Z$^b$—R$^b$) at the 1-position, 3-position, 6-position, and/or 8-position of the aromatic rings in the general formula (9) and, when Y$^1$=S, making Y$^1$ into —SO$_2$— by oxidation.

[Chemical Formula 4]

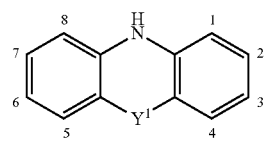

(9)

(where, in the general formula (9), Y$^1$ is S or a chemical single bond)

As the reaction method which introduces one or two substituents (—Z$^a$—R$^a$, —Z$^b$—R$^b$) at the 1-position, 3-position, 6-position, and/or 8-position of the aromatic rings in the general formula (9), for example, a reaction which causes the formation of a carbon-carbon bond at the carbon atoms of the 1-position, 3-position, 6-position, and/or 8-position of the aromatic rings in the general formula (9) (this reaction method will be referred to as the "reaction method α"), a reaction which causes the formation of a carbon-SO$_2$ bond at the carbon atoms of the 1-position, 3-position, 6-position, and/or 8-position of the aromatic rings in the general formula (9) (this reaction method will be referred to as the "reaction method β"), a reaction which causes the formation of a carbon-sulfur bond at the carbon atoms of the 1-position, 3-position, 6-position, and/or 8-position of the aromatic rings in the general formula (9) (this reaction method will be referred to as the "reaction method γ"), etc. may be mentioned.

Below, the method of production of the compound which is expressed by the general formula (1) will be explained in detail while using as an example the case of using compounds which are expressed by the general formula (9) as a starting material and using the methods of the above-mentioned reaction method α, reaction method β, and reaction method γ.

[A. Method of Production (1) Using Reaction Method α]

The reaction formula of the method of production (1) which uses the reaction method α is shown below. Note that, in the following reaction formula, among the compounds which are expressed by the general formula (1), the case where Y is a chemical single bond or —SO$_2$—, n or m is 0, and or —Z$^b$—R$^b$ is a group which is indicated by the formula: —C(CH$_3$)(r)-Ar (wherein, r indicates a hydrogen atom or alkyl group, and Ar indicates a substitutable phenyl group) is illustrated.

[Chemical Formula 5]

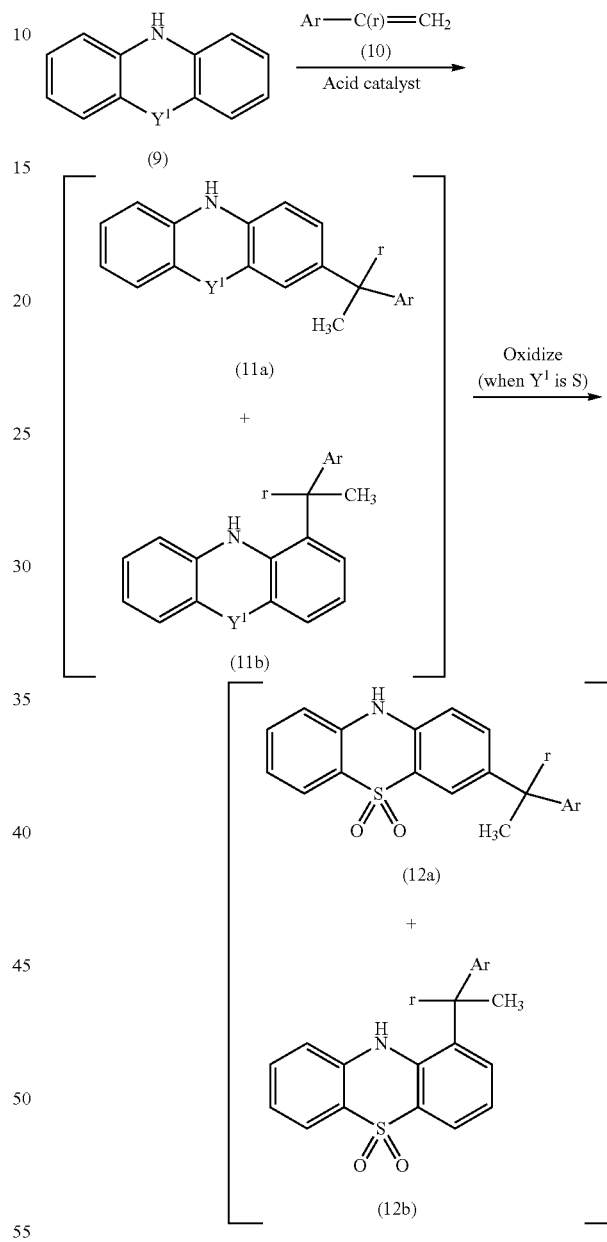

Further, in accordance with the above reaction formula, among the compounds which are expressed by the general formula (1), a compound where Y is a chemical single bond can be obtained as a compound which is shown in the general formula (11a) and/or (11b) by using a compound which is expressed by the general formula (9) (carbazole where Y$^1$=chemical single bond) as a starting material and reacting the styrene compound which is expressed by the general formula (10) in the presence of an acid catalyst.

Further, in accordance with the above reaction formula, among the compounds which are expressed by the general formula (1), a compound where Y is —SO$_2$— can be obtained as a compound which is shown in the general formula (12a) and/or (12b) by using a compound which is expressed by the general formula (9) (phenothiazine where Y$^1$=S) as a starting material, reacting the styrene compound which is expressed by the general formula (10) in the presence of an acid catalyst, and oxidizing the compound which is obtained by the reaction (compound which is shown in the general formula (11a) and/or (11b)).

Note that, as specific examples of a compound which is expressed by the general formula (10) which is used for the above reaction, styrene; alkylated styrene such as 4-methylstyrene, α-methylstyrene, 4,α-dimethylstyrene, 2,4-dimethylstyrene, ethylstyrene, and p-t-butylstyrene; halogenated styrene such as 2-chlorostyrene, and 2,4-dichlorostyrene; etc. may be mentioned. Further, the amount of use of the compound which is expressed by the general formula (10) is 0.5 to 1.5 moles per 1 mole of the compound which is expressed by the general formula (9).

As specific examples of an acid catalyst which is used for the reaction, sulfonic acids such as methanesulfonic acid, phenylsulfonic acid, and p-toluenesulfonic acid; inorganic acids such as hydrochloric acid, and sulfuric acid; etc. may be mentioned. The acid catalyst is usually charged at the time of start of the reaction, but may also be added in the middle of the reaction. The amount of use of the acid catalyst is usually 0.005 to 0.5 mole per 1 mole of the compound which is expressed by the general formula (9), preferably 0.01 to 0.3 mole, more preferably 0.02 to 0.1 mole.

The above reaction can be performed in a suitable solvent. The solvent which is used is not particularly limited so long as being inert to the reaction, but, for example, aromatic hydrocarbon-based solvent such as benzene, toluene, and xylene; aliphatic hydrocarbon-based solvent such as n-pentane, n-hexane, n-octane, cyclopentane, and cyclohexane; halogenated hydrocarbon-based solvent such as 1,2-dichloroethane, and monochlorobenzene; etc. may be mentioned. These solvents may be used as single type alone or as two or more types combined. The amount of use of the solvent depends on the reaction scale etc., but is 1 ml to 100 ml per 1 g of the compound which is expressed by the general formula (9).

Further, in the compound which is expressed by the general formula (9), when Y$^1$=S, the oxidizing agent which is used for oxidation is not particularly limited. Organic peroxide such as acetic acid-hydrogen peroxide, and m-chloroperbenzoic acid may be mentioned. The amount of use of the oxidizing agent is 2 to 5 moles per 1 mole of the compound which is expressed by the general formula (11a) or (11b).

Such an oxidation reaction can be performed in a suitable solvent. The solvent which is used is not particularly limited so long as being inert to the reaction, but, for example, aromatic hydrocarbon-based solvent such as benzene, toluene, and xylene; aliphatic hydrocarbon-based solvent such as n-pentane, n-hexane, n-octane, cyclopentane, and cyclohexane; halogenated hydrocarbon-based solvent such as dichloromethane, chloroform, 1,2-dichloroethane, and monochlorobenzene; acetic acid; etc. may be mentioned. These solvents may be used as single type alone or as two or more types combined. The amount of use of the solvent depends in the reaction scale etc., but is 1 ml to 100 ml per 1 g of the compound which is expressed by the general formula (11a) or (11b).

Furthermore, such an oxidation reaction can also be performed continuously by adding to a reaction solution which includes a compound which is expressed by the general formula (11a) and/or (11b) predetermined amounts of acetic acid and hydrogen peroxide.

[B. Method of Production (2) Using Reaction Method α]

The reaction formula of the method of production (2) which uses the reaction method α is shown below. Note that, in the following reaction formula, the case where, in the compound which is expressed by the general formula (1), Y is a chemical single bond or —SO$_2$—, n and m are 1, and —Z$^a$—R$^a$ and —Z$^b$—R$^b$ are groups which are shown by the formula: —C(CH$_3$)(r)-Ar (wherein, r indicates a hydrogen atom or alkyl group, and Ar indicates a substitutable phenyl group) is illustrated.

[Chemical Formula 6]

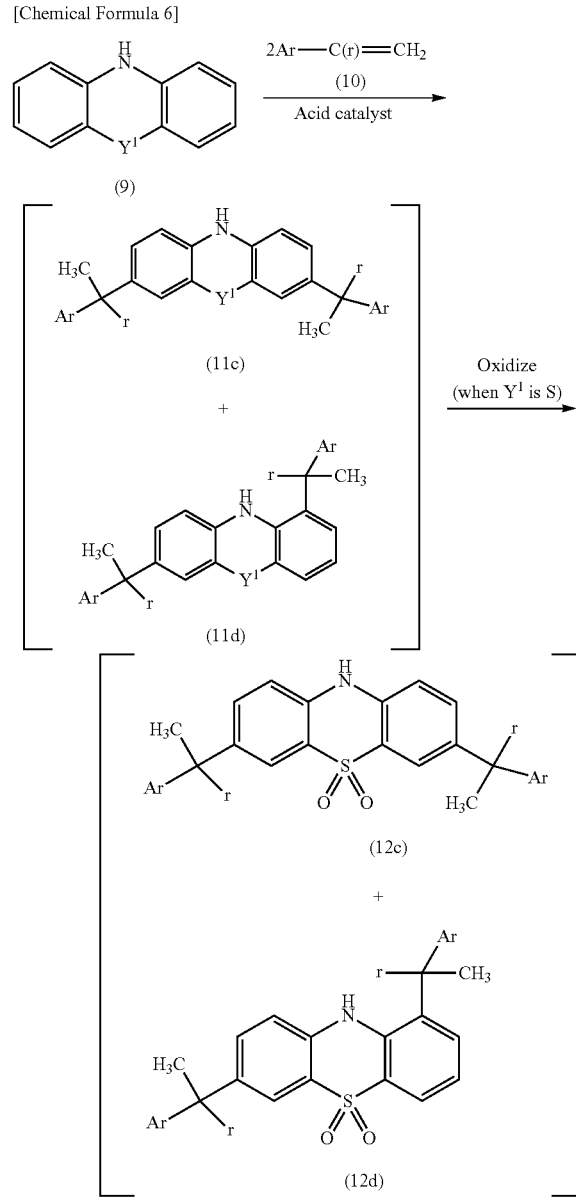

Further, in accordance with the above reaction formula, in the compound which is expressed by the general formula (1), the compound where Y is a chemical single bond can be obtained as a compound of the general formula (11c) and/or (11d) by using the compound which is expressed by the general formula (9) (carbazole where Y$^1$=chemical single bond) as a starting material and reacting the styrene compound which is expressed by the general formula (10) in the presence of an acid catalyst.

Further, in accordance with the above reaction formula, in the compound which is expressed by the general formula (1), the compound where Y is —SO$_2$— can be obtained as a compound of the general formula (12c) and/or (12d) by using the compound which is expressed by the general formula (9) (phenothiazine where Y$^1$=S) as a starting material, reacting the styrene compound which is expressed by the general formula (10) in the presence of an acid catalyst, and oxidizing the compound which is obtained by the reaction (the compound which is shown by the general formula (11c) and/or (11d)).

Note that, in the above reaction, as the compound which is expressed by the general formula (10), acid catalyst, solvent, and oxidizing agent, ones similar to the above-mentioned method of production (1) which uses the reaction method a can be used. Further, for the amounts of use of these, except for making the amount of use of the compound which is expressed by the general formula (10) 2 to 3 moles per 1 mole of the compound which is expressed by the general formula (9) and making the amount of use of the oxidizing agent 2 to 10 moles per 1 mole of the compound which is expressed by the general formula (11c) or (11d), similar amounts to the above-mentioned method of production (1) which uses the reaction method a can be used.

[C. Method of Production Using Reaction Method β]

The reaction formula of the method of production which uses the reaction method 3 is shown below. Note that, in the following reaction formula, the case where, in the compound which is expressed by the general formula (1), Y is a chemical single bond or —SO$_2$—, n or m are 0, and —Z$^a$—R$^a$ or —Z$^b$—R$^b$ are groups which are shown by the formula: —SO$_2$—Ar (wherein, Ar indicates a substitutable phenyl group) is illustrated.

[Chemical Formula 7]

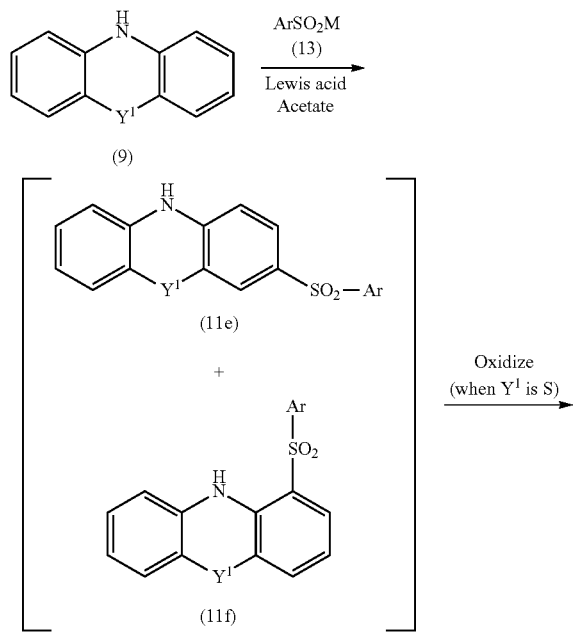

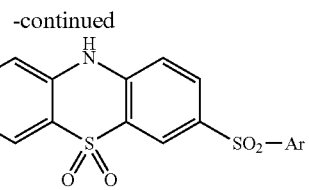

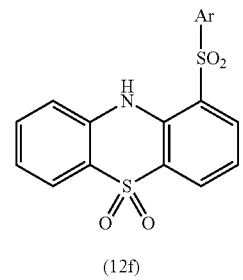

Further, in accordance with the above reaction formula, in the compound which is expressed by the general formula (1), the compound where Y is a chemical single bond can be obtained as a compound of the general formula (11e) and/or (11f) by using the compound which is expressed by the general formula (9) (carbazole where Y$^1$=chemical single bond) as a starting material and reacting the sulfinate which is expressed by the general formula (13) in the presence of Lewis acid such as ferric chloride and acetate such as potassium acetate (M expressed sodium or other alkali metal).

Further, in accordance with the above reaction formula, in the compound which is expressed by the general formula (1), the compound where Y is —SO$_2$— can be obtained as a compound of the general formula (12e) and/or (12f) by using the compound which is expressed by the general formula (9) (phenothiazine where Y$^1$=S) as a starting material, reacting the sulfinate which is expressed by the general formula (13) in the presence of Lewis acid such as ferric chloride and acetate such as potassium acetate, and oxidizing the compound which is obtained by the reaction (compound which is shown by the general formula (11e) and/or (11f)).

As the sulfinate which is expressed by the general formula (13) which is used for the reaction, sodium phenylsulfinate, potassium phenylsulfinate, sodium p-toluenesulfinate, potassium p-toluenesulfinate, etc. may be mentioned. Further, the amount of use of the compound which is expressed by the general formula (13) is 0.5 to 1.5 moles per 1 mole of the compound which is expressed by the general formula (9).

In the reaction, the amount of use of the Lewis acid is usually 5 to 10 moles per 1 mole of the compound which is expressed by the general formula (9), while the amount of use of the acetate is usually 1 to 3 moles per 1 mole of the compound which is expressed by the general formula (9).

The reaction can be performed in a suitable solvent. The solvent which is used is not particularly limited so long as being inert to the reaction, but, for example, alcohol-based solvent such as methyl alcohol, ethyl alcohol, propyl alcohol, and isopropyl alcohol may be mentioned. The solvent which is used can be used as single type alone or as two or more types combined. The amount of use of the solvent depends on the reaction scale etc., but is 1 ml to 100 ml per 1 g of the compound which is expressed by the general formula (9).

Note that, in the compound which is expressed by the general formula (9), when $Y^1$=S, the oxidation reaction can be performed in the same way as the above-mentioned method of production (1) which uses the reaction method α.

[D. Method of Production Using Reaction Method γ]

The reaction formula of the method of production which uses the reaction method γ is shown below. Note that, in the following reaction formula, the case where, in the compound which is expressed by the general formula (1), Y is a chemical single bond, n and m are 1, and —$Z^a$—$R^a$ or —$Z^b$—$R^b$ are groups which are shown by the formula: —$SO_2$—R (wherein, R expresses a $C_1$ to $C_{30}$ organic group) is illustrated.

[Chemical Formula 8]

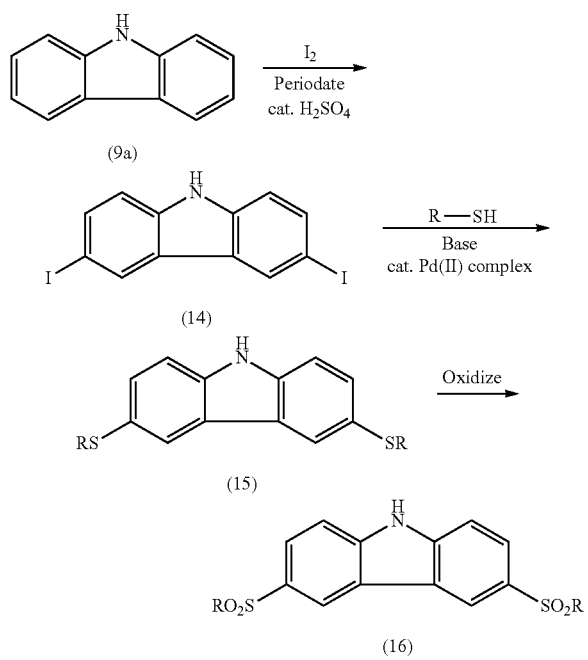

Further, in accordance with the above reaction formula, a compound which is expressed by the general formula (9a) (carbazole) can be used as a starting material and iodine can be reacted in the presence of periodate and a catalytic amount of sulfuric acid to obtain diiodo which is expressed by the general formula (14), then the obtained diiodo can be reacted with mercaptan which is expressed by the formula: R—SH (wherein, R indicates a $C_1$ to $C_{30}$ organic group) in the presence of a base and a catalytic amount of palladium (II) complex so as to obtain the compound which is expressed by the general formula (15), then the obtained compound can be oxidized to obtain a compound which is expressed by the general formula (16).

Note that, in the above reaction, as specific examples of a periodate which is used for the reaction which obtains the diiodo which is shown in the general formula (14), sodium periodate, potassium periodate, etc. may be mentioned. The amount of use of the periodate is 0.1 mole to 1 mole epr 1 mole of the compound which is expressed by the general formula (9a). Further, the amount of use of iodine is 1 mole to 3 moles per 1 mole of the compound which is expressed by the general formula (9a).

The reaction which obtains the diode can be performed in a suitable solvent. The solvent which is used is not particularly limited so long as being inert to the reaction, but for example, alcohol-based solvent such as methyl alcohol, ethyl alcohol, n-propyl alcohol, and isopropyl alcohol may be mentioned. The solvent which is used can be used as single type alone or as two or more types combined. The amount of use of the solvent depends on the reaction scale etc., but is 1 ml to 100 ml per 1 g of the compound which is expressed by the general formula (9a).

Further, in the reaction, as specific examples of a mercaptan which is used for the reaction for obtaining the compound which is expressed by the general formula (15), thiophenol, p-toluenethiol, benzylmercaptan, α-methylbenzylmercaptan, α,α-dimethylmercaptan, t-butylmercaptan, etc. may be mentioned. The amount of use of the mercaptan is 1 mole to 3 moles per 1 mole of the compound which is expressed by the general formula (14).

As the base which is used for the reaction for obtaining the compound which is expressed by the general formula (15), metal alkoxide such as sodium t-butoxide, and potassium t-butoxide; organic base such as DBU (1,8-diazabicyclo [5.4.0]undeca-7-ne), and DABCO (1,4-diazabicyclo[2.2.2] octane); etc. may be mentioned. The amount of use of the base is usually 1 mole to 10 moles per 1 mole of compound which is expressed by the general formula (14).

As specific examples of a palladium (II) complex which is used for the reaction for obtaining the compound which is expressed by the general formula (15), [1,1'-bis(diphenylphosphino)ferrocene]palladium (II)dichloride dichloromethane adduct etc. may be mentioned.

The reaction for obtaining the compound which is expressed by the general formula (15) can be performed in a suitable solvent. The solvent which is used is not particularly limited so long as being inert to the reaction, but for example, aromatic hydrocarbon-based solvent such as benzene, toluene, and xylene; aliphatic hydrocarbon-based solvent such as n-pentane, n-hexane, n-octane, cyclopentane, and cyclohexane; halogenated hydrocarbon-based solvent such as dichloromethane, chloroform, 1,2-dichloroethane, and monochlorobenzene; etc. may be mentioned. These solvents can be used as single type alone or as two or more types combined. The amount of use of the solvent depends on the reaction scale etc., but is 1 ml to 100 ml per 1 g of the compound which is expressed by the general formula (14).

The oxidizing agent which is used for the oxidation reaction for obtaining the compound which is expressed by the general formula (16) is not particularly limited, but organic peroxide such as acetic acid-hydrogen peroxide, and m-chloroperbenzoic acid may be mentioned. The amount of use of the oxidizing agent is 2 to 10 moles per 1 mole of the compound which is expressed by the general formula (15).

As the suitable solvent for such an oxidation reaction, a solvent similar to the one used in the oxidation reaction of the above-mentioned method of production (1) which uses the reaction method a may be used.

Furthermore, such an oxidation reaction can be performed continuously by adding to a reaction solution which contains the compound which is expressed by the general formula (15) predetermined amounts of acetic acid and hydrogen peroxide.

Each of the reactions of the above reaction method α, reaction method β, and reaction method γ proceeds smoothly in the temperature range from 0° C. up to the boiling point of the solvent which is used. The reaction time is usually several minutes to several hours. Further, in each reaction method, after the end of the reaction, the usual post-treatment operations in organic synthetic chemicals are performed. If desired, the column chromatography, recrystallization method, distillation method, and other known separating and refining means can be applied to isolate the target substance. The structure of the target substance can be identified by measurement of the NMR spectrum, IR spectrum, mass spectrum, etc. and by elementary analysis etc.

In the acrylic rubber composition of the present invention, the content of the compound which is expressed by the general formula (1) is, with respect to 100 parts by weight of the acrylic rubber, 0.1 to 50 parts by weight, preferably 0.3 to 15 parts by weight, more preferably 0.3 to 5 parts by weight, furthermore preferably 0.4 to 4.5 parts by weight, particularly preferably 0.5 to 2.5 parts by weight. If the content of the compound which is expressed by the general formula (1) is within the above range, even if the obtained cross-linked rubber product is exposed long term to high temperature conditions, a drop in the elongation and other physical properties can be suppressed and the heat resistance is excellent. On the other hand, if the content of the compound which is expressed by the general formula (1) is too small, the obtained cross-linked rubber product is liable to drop in heat resistance, while if too great, bleedout of the compound which is expressed by the general formula (1), a drop in the physical properties of the cross-linked rubber product, and discoloration of the molded product may occur. The compound which is expressed by the general formula (1) can be used as single type alone or as two or more types combined.

Further, in the acrylic rubber composition of the present invention, as an antiaging agent, in addition to the compound which is expressed by the general formula (1), at least one type of another antiaging agent other than the compound which is expressed by the general formula (1) may be contained.

The other antiaging agent which is used in the present invention is not particularly limited, but an amine-based antiaging agent excluding the compound which is expressed by the general formula (1), a phenol-based antiaging agent, sulfur-based antiaging agent, and phosphor-based antiaging agent are preferable. The acrylic rubber composition of the present invention preferably contains at least one type of antiaging agent which is selected from the other antiaging agents.

The amine-based antiaging agent excluding the compound which is expressed by the general formula (1) is not particularly limited, but diphenylamine-based antiaging agent such as octylated diphenylamine, dioctylated diphenylamine, 4,4'-bis($\alpha,\alpha$-dimethylbenzyl)diphenylamine, p-(p-toluenesulfonylamide)diphenylamine, a reaction product of diphenylamine and acetone, a reaction product of diphenylamine and isobutylene, a reaction product of diphenylamine, and acetone and aniline, and an alkylated diphenylamine; p-phenylenediamine-based antiaging agent such as N,N'-diphenyl-p-phenylenediamine, N-isopropyl-N'-phenyl-p-phenylenediamine, N,N'-di-2-naphthyl-p-phenylenediamine, N-cyclohexyl-N'-phenyl-p-phenylenediamine, N-phenyl-N'-(3-methacryloyloxy-2-hydroxypropyl)-p-phenylenediamine, N,N'-bis(1-methylheptyl)-p-phenylenediamine, N,N'-bis(1,4-dimethylpentyl)-p-phenylenediamine, N,N'-bis(1-ethyl-3-methylpentyl)-p-phenylenediamine, N-(1,3-dimethylbutyl)-N'-phenyl-p-phenylenediamine, diallyl-p-phenylenediamine in mixture, and phenylhexyl-p-phenylenediamine; naphthylamine-based antiaging agent such as phenyl-$\alpha$-naphthylamine, and phenyl-$\beta$-naphthylamine; quinoline-based antiaging agent such as 2,2,4-trimethyl-1,2-dihydroquinoline, and 6-ethoxy-2,2,4-trimethyl-1,2-dihydroquinoline; etc. may be mentioned. Among these as well, a diphenylamine-based antiaging agent and p-phenylenediamine-based antiaging agent are preferable.

The phenol-based antiaging agent is not particularly limited, but monophenol-based antiaging agent such as 2,6-di-t-butyl-p-cresol, 2,6-di-t-butyl-4-ethyl phenol, 2,6-di-t-butyl-4-methylphenol, 2,6-di-t-butyl-4-sec-butylphenol, 2-(1-methylcyclohexyl)-4,6-dimethylphenol, 2,6-di-t-butyl-$\alpha$-dimethylamino-p-cresol, 2,4-bis[(octylthio)methyl]-o-cresol, styrenated phenol, and alkylated phenol; bis, tris, or polyphenol-based antiaging agent such as 2,2'-methylene bis(4-methyl-6-t-butylphenol), 2,2'-methylene bis(4-ethyl-6-t-butylphenol), 4,4'-methylene bis(2,6-di-t-butylphenol), 2,2'-methylene bis(6-$\alpha$-methylbenzyl-p-cresol), methylene-cross-linked polyvalent alkylphenol, 4,4'-butylidene bis(6-t-butyl-m-cresol), 4,4'-butylidene bis(3-methyl-6-t-butylphenol), 2,2'-ethylidene bis(4,6-di-t-butylphenol), 1,1-bis-(4-hydroxyphenyl)cyclohexane, 2,2'-dihydroxy-3,3'-($\alpha$-methylcyclohexyl)-5,5'-dimethyldiphenylmethane, alkylated bisphenol, butylated reaction products of p-cresol and dicyclopentadiene, 2,5-di-t-butylhydroquinone, and 2,5-di-t-amylhydroquinone; thiobisphenol-based antiaging agent such as 4,4'-thiobis(6-t-butyl-m-cresol), 4,4'-thiobis(6-t-butyl-o-cresol), 4,4'-thiobis(3-methyl-6-t-butylphenol), and bis (3,5-di-t-butyl-4-hydroxybenzyl)sulfide; etc. may be mentioned. Among these as well, a monophenol-based antiaging agent and bisphenol-based antiaging agent are preferable.

The sulfur-based antiaging agent is not particularly limited, but dialkyl thiodipropionate antiaging agent such as dilauryl thiodipropionate, and distearyl thiodipropionate; organic thio acid-based antiaging agent such as dilauryl thiodipropionate, and nickel isopropyl xantogenate; benzimidazole-based antiaging agent such as 2-mercaptobenzimidazole, 2-mercaptomethylbenzimidazole, 2-mercaptobenzimidazole and phenol condensates in mixture, zinc salt of 2-mercaptobenzimidazole, zinc salt of 2-mercaptomethylbenzimidazole, and, 4- and 5-mercaptomethylbenzimidazole; dithiocarbamate-based antiaging agent such as nickel dimethyl dithiocarbamate, nickel diethyl dithiocarbamate, nickel dibutyl dithiocarbamate, and nickel diisobutyl dithiocarbamate; thiourea-based antiaging agent such as 1,3-bis(dimethylamino-propyl)-2-thiourea, and tributylthiourea; etc. may be mentioned. Among these as well, a benzimidazole-based antiaging agent is preferable.

The phosphor-based antiaging agent is not particularly limited, but phosphorus acid ester-based antiaging agent such as triphenyl phosphite, diphenylisooctyl phosphite, diphenylisodecyl phosphite, diphenylnonylphenyl phosphite, triisodecyl phosphite, tris(nonylphenyl)phosphite, tris(2,4-di-t-butylphenyl)phosphite, 4,4'-butylidenebis(3-methyl-6-t-butylditridecylphosphite), 2,2'-ethylidene bis(3-methyl-6-t-butylphenol)fluoro phosphite, and 4,4'-isopropylidene-diphenolalkyl($C_{12}$ to $C_{18}$)phosphite; etc. may be mentioned. Among these as well, a phosphorus acid ester-based antiaging agent is preferable.

When the compound which is expressed by the general formula (1) and other antiaging agent are used together, the total content of the compound which is expressed by the general formula (1) and the other antiaging agent is, with respect to 100 parts by weight of acrylic rubber, 0.1 to 50 parts by weight, preferably 0.3 to 15 parts by weight, more preferably 0.3 to 5 parts by weight, furthermore preferably 0.4 to 4.5 parts by weight. The total content of the compound which is expressed by the general formula (1) and the other antiaging agent can be suitably set within the above range. If the total content of the compound which is expressed by the general formula (1) and the other antiaging agent is within the above range, even if the obtained cross-linked rubber product is exposed long term to high temperature conditions, the drop in the elongation and other physical properties can be suppressed and the heat resistance is excellent. On the other hand, if the total content of the compound which is expressed by the general formula (1) and the other antiaging agent is too small, the obtained cross-linked rubber product is liable to fall in heat resistance, while if too great, bleedout of the antiaging agent, a drop in the physical properties of the cross-linked rubber product, and discoloration of the molded product may occur. The other antiaging agent, like the compound which is expressed by the general formula (1), may be used as single type alone or as two or more types combined.

When using the compound which is expressed by the general formula (1) and the other antiaging agent together, as the ratio of content, by weight ratio of [compound which is expressed by the general formula (1):other antiaging agent], [1:0.1 to 1:30] is preferable, and [1:0.2 to 1:10] is more preferable.

<Cross-Linking Agent>

The cross-linking agent which is used in the present invention may be suitably selected in accordance with the type of the cross-linkable monomer which is contained in the above-mentioned acrylic rubber and the molding application of the acrylic rubber composition, but is not particularly limited if it is one which can cross-link the above-mentioned acrylic rubber. As such a cross-linking agent, for example, polyvalent amine compounds such as diamine compounds and their carbonates; sulfur; sulfur donors; triazinethiol compounds; polyvalnet epoxy compounds; organic carboxylic acid ammonium salts; dithiocarbamic acid metal salts; polyvalent carboxylic acids; quaternary onium salts; imidazole compounds; isocyanulic acid compounds; organic peroxides; and other conventional known cross-linking agents may be used. These cross-linking agents may be used as single type or two or more types combined.

Among these as well, when the acrylic rubber which is used in the present invention is a carboxyl group-containing acrylic rubber, as the cross-linking agent, a polyvalent amine compound and its carbonates are preferably used.

The polyvalent amine compound and its carbonates are not particularly limited, but $C_4$ to $C_{30}$ polyvalent amine compounds and their carbonates are preferable. As examples of such a polyvalent amine compound and its carbonates, aliphatic polyvalent amine compounds and their carbonates and aromatic polyvalent amine compounds etc. may be mentioned. On the other hand, compounds like guanidine compounds which have nonconjugated nitrogen-carbon double bonds are not included.

The aliphatic polyvalent amine compound and its carbonates are not particularly limited, but, for example, hexamethylenediamine, hexamethylenediamine carbamate, and N,N'-dicinnamyldene-1,6-hexanediamine, etc. may be mentioned. Among these as well, hexamethylenediamine carbamate is preferable.

The aromatic polyvalent amine compound is not particularly limited, but, for example, 4,4'-methylene dianiline, p-phenylenediamine, m-phenylenediamine, 4,4'-diaminodiphenyl ether, 3,4'-diaminodiphenyl ether, 4,4'-(m-phenylenediisopropylidene)dianiline, 4,4'-(p-phenylenediisopropylidene)dianiline, 2,2'-bis[4-(4-amino phenoxy)phenyl]propane, 4,4'-diaminobenzanilide, 4,4'-bis(4-amino phenoxy)biphenyl, m-xylylenediamine, p-xylylenediamine, 1,3,5-benzenetriamine, etc. may be mentioned. Among these as well, 2,2'-bis[4-(4-amino phenoxy)phenyl]propane is preferable.

When the acrylic rubber which is used in the present invention is an epoxy group-containing acrylic rubber, as the cross-linking agent, aliphatic polyvalent amine compounds such as hexamethylenediamine, and hexamethylenediamine carbamate, and their carbonates; aromatic polyvalent amine compounds such as 4,4'-methylenedianiline; ammonium carboxylic acid salts such as ammonium benzoate, and ammonium adipate; dithiocarbamic acid metal salts such as zinc dimethyldithiocarbamate; polyvalent carboxylic acids such as tetradecane diacid; quaternary onium salts such as cetyltrimethylammonium bromide; imidazole compounds such as 2-methylimidazole; isocyanulic acid compounds such as ammonium isocyanulate; etc. may be used. Among these as well, ammonium carboxylic acid salts and dithiocarbamic acid metal salts are preferable, while ammonium benzoate is more preferable.

When the acrylic rubber which is used in the present invention is a halogen atom-containing acrylic rubber, as the cross-linking agent, use of sulfur, a sulfur donor, or a triazinethiol compound is preferable.

As specific examples of a sulfur donor, dipentamethylenethiuram hexasulfide, triethylthiuram disulfide, etc. may be mentioned.

As specific examples of a triazinethiol compound, 1,3,5-triazine-2,4,6-trithiol, 6-anilino-1,3,5-triazine-2,4-dithiol, 6-dibutylamino-1,3,5-triazine-2,4-dithiol, 6-diallylamine-1,3,5-triazine-2,4-dithiol, and 6-octylamino-1,3,5-triazine-2,4-dithiol, etc. may be mentioned, but among these as well, 1,3,5-triazine-2,4,6-trithiol is preferable.

Furthermore, when the acrylic rubber which is used in the present invention is a carboxyl group- and halogen atom-containing acrylic rubber, when making carboxyl groups the cross-linking points, polyvalent amine compounds and their carbonates are preferable. Further, when making the halogen atoms the cross-linking points, sulfur, a sulfur donor, or triazinethiol compound are preferable. These cross-linking agents can be used as single type alone or as two or more types combined. A cross-linking agent which is suitable when making the carboxyl groups the cross-linking points and a cross-linking agent which is suitable when making the halogen atoms the cross-linking points can be used together. Note that, as specific examples of a polyvalent amine compound and its carbonates, sulfur donor, and triazinethiol compound, the above-mentioned ones may be mentioned.

Further, the acrylic rubber which is used in the present invention contains ethylene-acrylate rubber in 0.1 to 100 wt % and when the acrylic rubber which contains the ethylene-acrylate rubber has carboxyl groups as cross-linking points, as the cross-linking agent, ones similar to the case of the above-mentioned carboxyl group-containing acrylic rubber can be used.

In the acrylic rubber composition of the present invention, the content of the cross-linking agent is, with respect to 100 parts by weight of the acrylic rubber, 0.05 to 20 parts by weight, preferably 0.1 to 15 parts by weight, more preferably 0.3 to 12 parts by weight. If the content of the cross-linking agent is in the range, the cross-linking is sufficiently performed and the obtained cross-linked rubber product is excellent in mechanical properties. On the other hand, if the content of the cross-linking agent is too small, the cross-linking becomes insufficient and the obtained cross-linked rubber product becomes poor in shape retention in some cases, while if too great, the obtained cross-linked rubber product becomes too hard in some cases.

<Cross-Linking Accelerator>

Further, the acrylic rubber composition of the present invention preferably further contains a cross-linking accelerator.

The cross-linking accelerator is not particularly limited, but when the above-mentioned acrylic rubber is a carboxyl group-containing acrylic rubber and the cross-linking agent is a polyvalent amine compound or its carbonate, an aliphatic monovalent secondary amine compound, aliphatic monovalent ternary amine compound, guanidine compound, imidazole compound, quaternary onium salt, ternary phosphine compound, alkali metal salt of a weak acid, diazabicycloalkene compound, etc. are preferably used. These cross-linking accelerators may be used as single type or as two or more types combined.

When the acrylic rubber which is used in the present invention is an epoxy group-containing acrylic rubber and the cross-linking agent is a dithiocarbamic acid metal salt, as the cross-linking accelerator, another dithiocarbamic acid metal salt other than the dithiocarbamic acid metal salt which was used as the cross-linking agent is preferably used. These cross-linking accelerators can be used as single type or two or more types combined.

When the acrylic rubber which is used in the present invention is a halogen atom-containing acrylic rubber and the cross-linking agent is sulfur or a sulfur donor, as the cross-linking accelerator, an aliphatic acid metal soap etc. are preferably used. Further, when the acrylic rubber which is used in the present invention is a halogen atom-containing acrylic rubber and the cross-linking agent is a triazinethiol compound, as the cross-linking accelerator, a dithiocarbamate and its derivatives, thiourea compound, thiuram sulfide compound, etc. are preferably used. These cross-linking accelerator can be used as single type or as two or more types combined.

Furthermore, when the acrylic rubber which is used in the present invention is a carboxyl group- and halogen atom-containing acrylic rubber and the cross-linking agent is a polyvalent amine compound or its carbonate, as the cross-linking accelerator, an aliphatic monovalent secondary amine compound, aliphatic monovalent ternary amine compound, guanidine compound, imidazole compound, quaternary onium salt, ternary phosphine compound, alkali metal salt of a weak acid, diazabicycloalkene compound, etc. are preferably used. When the acrylic rubber which is used in the present invention is a carboxyl group- and halogen atom-containing acrylic rubber and the cross-linking agent is sulfur or a sulfur donor, as the cross-linking accelerator, an aliphatic acid metal soap etc. are preferably used. Furthermore, when the acrylic rubber which is used in the present invention is a carboxyl group- and halogen atom-containing acrylic rubber and the cross-linking agent is a triazinethiol compound, as the cross-linking accelerator, a dithiocarbamate and its derivatives, thiourea compound, and thiuram sulfide compound, etc. are preferably used. These cross-linking accelerators can be used as single type alone or as two or more types combined. A cross-linking agent which is suitable when making the carboxyl groups the cross-linking points and a cross-linking agent which is suitable when making the halogen atoms the cross-linking points can be used together.

Further, the acrylic rubber which is used in the present invention contains ethylene-acrylate rubber in 0.1 to 100 wt % and in the case that acrylic rubber which contains the ethylene-acrylate rubber has carboxyl groups as cross-linking points, when the cross-linking agent is a polyvalent amine compound or its carbonate, an aliphatic monovalent secondary amine compound, aliphatic monovalent ternary amine compound, guanidine compound, imidazole compound, quaternary onium salt, ternary phosphine compound, alkali metal salt of a weak acid, diazabicycloalkene compound, etc. are preferably used. These cross-linking accelerators can be used as single type or as two or more types combined.

An aliphatic monovalent secondary amine compound is a compound where two of the hydrogen atoms of ammonia are substituted by aliphatic hydrocarbon groups. The aliphatic hydrocarbon groups which are substituted for the hydrogen atoms are preferably $C_1$ to $C_{30}$ groups, more preferably $C_8$ to $C_{20}$ groups. As specific examples of aliphatic monovalent secondary amine compounds, dimethylamine, diethylamine, di-n-propylamine, diallylamine, diisopropylamine, di-n-butylamine, di-t-butylamine, di-sec-butylamine, didecylamine, diheptylamine, dioctylamine, dinonylamine, didecylamine, diundecylamine, didodecylamine, ditridecylamine, ditetradecylamine, dipentadecylamine, dicetylamine, di-2-ethyl hexylamine, dioctadecylamine, di-cis-9-octadecenylamine, dinonadecylamine, etc. may be mentioned. Among these as well, dioctylamine, didecylamine, didodecylamine, ditetradecylamine, dicetylamine, dioctadecylamine, di-cis-9-octadecenylamine, dinonadecylamine, etc. are preferable.

An aliphatic monovalent ternary amine compound is a compound in which all of the three hydrogen atoms of ammonia are substituted by aliphatic hydrocarbon groups. The aliphatic hydrocarbon groups which are substituted for the hydrogen atoms are preferably $C_1$ to $C_{30}$ groups, more preferably $C_1$ to $C_{22}$ groups. As specific examples of an aliphatic monovalent ternary amine compounds, trimethylamine, triethylamine, tri-n-propylamine, triallylamine, triisopropylamine, tri-n-butylamine, tri-t-butylamine, tri-sec-butylamine, trihexylamine, triheptylamine, trioctylamine, trinonylamine, tridecylamine, triundecylamine, tridodecylamine, tritridecylamine, tritetradecylamine, tripentadecylamine, tricetylamine, tri-2-ethylhexylamine, trioctadecylamine, tri-cis-9-octadecenylamine, trinonadecylamine, N,N-dimethyldecylamine, N,N-dimethyldodecylamine, N,N-dimethyltetradecylamine, N,N-dimethyl-cetylamine, N,N-dimethyloctadecylamine, N,N-dimethylbehenylamine, N-methyldidecylamine, N-methyldidodecylamine, N-methylditetradecylamine, N-methyldicetylamine, N-methyldioctadecylamine, N-methyldibehenylamine, dimethylcyclohexylamine, etc. may be mentioned. Among these as well, N,N-dimethyldodecylamine, N,N-dimethyltetradecylamine, N,N-dimethylcetylamine, N,N-dimethyloctadecylamine, N,N-dimethylbehenylamine, etc. are preferable.

As specific examples of a guanidine compound, 1,3-di-o-tolylguanidine, 1,3-diphenylguanidine, etc. may be mentioned, and 1,3-di-o-tolylguanidine is preferable.

As specific examples of an imidazole compound, 2-methylimidazole, 2-phenylimidazole, etc. may be mentioned.

As specific examples of a quaternary onium salt, tetra n-butylammonium bromide, octadecyltri n-butylammonium bromide, etc. may be mentioned.

As specific examples of a ternary phosphine compound, triphenylphosphine, tri-p-tolylphosphine, etc. may be mentioned.

As specific examples of an alkali metal salt of a weak acid, phosphates, carbonates, and other inorganic weak acid salts of sodium and potassium and stearates, laureates, and other organic weak acid salts of sodium and potassium may be mentioned.

As specific examples of a diazabicycloalkene compound, 1,8-diazabicyclo[5.4.0]unde-7-cene, 1,5-diazabicyclo[4.3.0] no-5-nene, etc. may be mentioned.

As specific examples of an aliphatic acid metal soap, sodium stearate, potassium stearate, potassium oleate, sodium laurate, sodium 2-ethyl hexanoate, etc. may be mentioned.

As specific examples of a dithiocarbamate and its derivatives, dithiocarbamic acid metal salt such as zinc dimethyldithiocarbamate, zinc diethyldithiocarbamate, zinc di-n-butyldithiocarbamate, zinc methylbenzyldithiocarbamate, zinc dibenzyldithiocarbamate, zinc methylcyclohexyldithiocarbamate, zinc N-pentamethylenedithiocarbamate, copper dimethyldithiocarbamate, lead dimethyldithiocarbamate, cadmium dimethyldithiocarbamate, bismuth dimethyldithiocarbamate, ferric dimethyldithiocarbamate, tellurium dimethyldithiocarbamate, and selenium dimethyldithiocarbamate; complex salts or double salts of dithiocarbamic acid metal salts and amines such as dibutylamine, and cyclohexylethyl amine; etc. may be mentioned. Among these as well, when the acrylic rubber is a halogen atom-containing acrylic rubber or a carboxyl group- and halogen atom-containing acrylic rubber and uses a cross-linking agent constituted by a triazinethiol compound, dithiocarbamic acid metal salts which use zinc are preferable and zinc di-n-butyldithiocarbamate is more preferable. On the other hand, when the acrylic rubber is an epoxy group-containing acrylic rubber and uses a cross-linking agent constituted by zinc dithiocarbamate, ferric dimethyldithiocarbamate is preferable.

As specific examples of a thiourea compound, N,N'-diphenylthiourea, N,N'-diethylthiourea, N,N'-dibutylthiourea, N,N'-diorthotolylthiourea, trimethylthiourea, ethylenethiourea, etc. may be mentioned. Among these as well, N,N'-diethylthiourea is preferable.

As specific examples of a thiuram sulfide compound, tetramethylthiuram monosulfide, tetramethylthiuram disulfide, tetraethylthiuram disulfide, tetra-n-butylthiuram disulfide, dipentamethylenethiuram tetrasulfide, etc. may be mentioned.

In the acrylic rubber composition of the present invention, the content of the cross-linking accelerator is, with respect to 100 parts by weight of the acrylic rubber, preferably 0.1 to 20 parts by weight, more preferably 0.2 to 15 parts by weight, furthermore preferably 0.3 to 10 parts by weight. If the content of the cross-linking accelerator in within the above range, the cross-linking is sufficiently performed, and the obtained cross-linked rubber product is excellent in mechanical properties. On the other hand, if the cross-linking accelerator is too small, the cross-linking does not sufficiently proceed and the obtained cross-linked rubber product may become inferior in mechanical properties, while if the cross-linking accelerator is too great, the cross-linking rate at the time of cross-linking becomes too fast and blooms of the cross-linking accelerator are liable to form at the surface of the obtained cross-linked rubber product or the cross-linked rubber product is liable to become too hard.

<Other Compounding Agents>

The acrylic rubber composition of the present invention may contain, in addition to the acrylic rubber, the compound which is expressed by the general formula (1), the cross-linking agent, the cross-linking accelerator which is used in accordance with need, and the antiaging agent other than the compound which is expressed by the general formula (1) which is used in accordance with need, compounding agents which are usually used in the field of rubber processing. As such compounding agents, for example, reinforcing fillers such as carbon black, and silica; nonreinforcing fillers such as calcium carbonate, and clay; photo stabilizers; scorch retarders; plasticizers; processing aids; slip agents; tackifiers; lubricants; flame retardants; antifungal agents; antistatic agents; coloring agents; silane coupling agents; cross-linking retardants; etc. may be mentioned. The amounts of these compounding agents are not particularly limited so long as in ranges not detracting from the object and effects of the present invention. Amounts in accordance with the purpose of compounding can be suitably blended.

Furthermore, the acrylic rubber composition of the present invention may have further blended into it, within ranges not detracting from the effect of the present invention, rubber other than the acrylic rubber which is used in the present invention, elastomers, resins, etc. For example, rubber such as natural rubber, polybutadiene rubber, polyisoprene rubber, styrene-butadiene rubber, acrylonitrile-butadiene rubber, silicone rubber, and fluorine rubber; elastomers such as olefin-based elastomers, styrene-based elastomers, vinyl chloride-based elastomers, polyester-based elastomers, polyamide-based elastomers, polyurethane-based elastomers, and polysiloxane-based elastomers; resins such as polyolefin-based resins, polystyrene-based resins, polyacryl-based resins, polyphenylene ether-based resins, polyester-based resins, polycarbonate-based resins, polyamide resins, vinyl chloride resins, and fluorine resins; etc. may be compounded. Note that, the total amount of the rubber other than acrylic rubber, elastomers, and resins is, with respect to 100 parts by weight of the acrylic rubber which is used in the present invention, preferably 50 parts by weight or less, more preferably 10 parts by weight or less, still more preferably 1 cart by weight or less.

<Method of Preparation of Acrylic Rubber Composition>

The acrylic rubber composition of the present invention is prepared by blending into the acrylic rubber the compound which is expressed by the general formula (1), the cross-linking agent, the cross-linking accelerator which is used in accordance with need, the other antiaging agent which is used in accordance with need, the other compounding agents, etc., mixing and kneading them by a Bambury mixer, kneader, etc., next, further kneading them by a kneading roll.

The order of blending in the ingredients is not particularly limited, but it is preferable to first fully mix the ingredients which are resistant to reaction or decomposition by heat, then mix in the ingredients which easily react or decompose due to heat such as the cross-linking agent or cross-linking accelerator etc. in a short time at a temperature at which the reaction or decomposition will not occur.

Further, among the ingredients, the compound which is expressed by the general formula (1) and the other antiaging agent which is used in accordance with need, for example, may be added to the polymer latex or polymer solution in advance and the polymer latex or polymer solution to which the compound which is expressed by the general formula (1) and the other antiaging agent which is used in accordance with need are added may be coagulated. Alternatively, the compound which is expressed by the general formula (1) and the other antiaging agent which is used in accordance with need may be added at any stage up to the step of producing the final product. Specifically, they may be blended in at any stage of the stage of production of the polymer pellets, the stage of kneading, or, furthermore, the stage of charging into the molding machine. The timing of blending them in can be suitably selected so as to enable sufficiently uniform dispersion in the polymer.

The acrylic rubber composition of the present invention has a Mooney viscosity ($ML_{1+4}$, 100° C.) (Compound Mooney) of preferably 10 to 100, more preferably 20 to 90, still more preferably 25 to 80.

<Cross-Linked Rubber>

The cross-linked rubber product of the present invention is obtained by cross-linking the above-mentioned acrylic rubber composition of the present invention.

The cross-linked rubber product of the present invention can be produced by using the acrylic rubber composition of the present invention, molding by a molding machine corresponding to the desired shape, for example, an extruder, an injection molding machine, a press, a roll, etc. and heating to cause a cross-linking reaction, and fixing the shape as cross-linked rubber product. In this case, it is possible to cross-link the rubber after molding it in advance or cross-link it simultaneously with the molding. The molding temperature is usually 10 to 200° C., preferably 25 to 120° C. The cross-linking temperature is usually 130 to 220° C., preferably 150 to 190° C., while the cross-linking time is usually 2 minutes to 10 hours, preferably 3 minutes to 5 hours. As the heating method, press heating, steam heating, oven heating, hot air heating, and other methods which are used for cross-linking rubber may be suitably selected.

Further, depending on the shape, size, etc. of the cross-linked rubber product, the cross-linked rubber product of the present invention may be further heated for secondary cross-linking. The secondary cross-linking differs depending on the heating method, cross-linking temperature, shape, etc., but preferably is performed for 1 to 48 hours. The heating method and the heating temperature may be suitably selected.

The thus obtained cross-linked rubber product of the present invention is obtained by using the above-mentioned acrylic rubber composition of the present invention, so is excellent in heat resistance and, even if exposed long term to high temperature conditions, can suppress a drop in elongation, compression set and other physical properties.

For this reason, the cross-linked rubber product of the present invention, making use of these characteristics, is suitable for use for various types of seals such as O-rings, packing, diaphragms, oil seals, shaft seals, bearing seals, mechanical seals, well head seals, seals for electrical and electronic equipment, and seals for pneumatic pressure equipment; various types of gaskets such as cylinder head gaskets which are attached to connecting parts of cylinder blocks and cylinder heads, rocker cover gaskets which are attached to connecting parts of rocker covers and cylinder heads, oil pan gaskets which are attached to connecting parts of oil pans and cylinder blocks or transmission cases, gaskets for fuel cell separators which are attached between pairs of housings sandwiching unit cells provided with anodes, electrolyte plates, and cathodes, and gaskets for top covers of hard disk drives; various types of belts; various hoses such as fuel hoses, turbo air hoses, oil hoses, radiator hoses, heater hoses, water hoses, vacuum brake hoses, control hoses, air-conditioner hoses, brake hoses, power steering hoses, air hoses, marine hoses, risers, and flow lines; various types of boots such as CVJ boots, propeller shaft boots, constant velocity joint boots, and rack and pinion boots; attenuation material rubber parts such as cushion materials, dynamic dampers, rubber couplings, air springs, and vibration insulators; etc. In particular, it is suitably used for extruded parts such as hoses which are used under severe high temperatures and seal member applications such as gaskets, seals.

EXAMPLES

Below, manufacturing examples of the compounds, manufacturing examples of the acrylic rubber, and examples, and comparative examples will be give to explain the present invention more specifically, but the present invention is not limited to these manufacturing examples and examples. Note that, in these examples, "parts" and "%" are based on weight unless particularly indicated otherwise.

Manufacturing Example 1

Synthesis of Compound 1

The following method was followed to synthesize the compound 1 which is shown in the following formula (17).

[Chemical Formula 9]

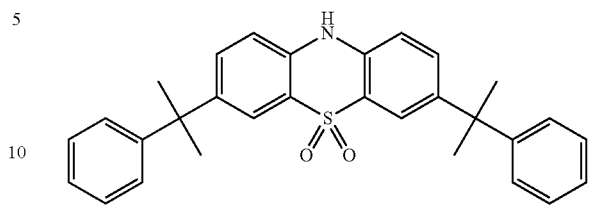

(17)

That is, first, a three-neck reactor equipped with a thermometer was charged, under a flow of nitrogen, with phenothiazine 50.0 g (250.92 mmol), then this was made to dissolve in toluene 200 ml. Next, to this solution, α-methylstyrene 59.31 g (501.83 mmol), p-toluenesulfonic acid monohydrate 1.19 g (6.27 mmol) were added and the mixture reacted at 80° C. for 1 hour. After that, the reaction solution was returned to room temperature, acetic acid 48 ml and 30% hydrogen peroxide solution 85.34 g (752.7 mmol) were added, and the mixture further reacted at 80° C. for 2 hours. The reaction solution was returned to room temperature, then charged into methanol 630 ml. Further, the precipitated crystal was filtered and rinsed by 320 ml of methanol to obtain a white crystal compound 1 in 85.7 g for a yield of 73%. The structure of the obtained compound 1 was identified by $^1$H-NMR. $^1$H-NMR (500 MHz, DMSO-d6, TMS, δppm): 1.67 (s, 12H), 7.15-7.32 (m, 12H), 7.43 (dd, 2H, J=9.0, 2.0 Hz), 7.68 (d, 2H, J=1.5 Hz), 10.84 (s, 1H).

Manufacturing Example 2

Synthesis of Compound 2

The following method was followed to synthesize the compound 2 of the following formula (18). Note that, when synthesizing the compound 2, this was synthesized by first obtaining the intermediate A which is shown by the following formula (19) and oxidizing the obtained intermediate A.

[Chemical Formula 10]

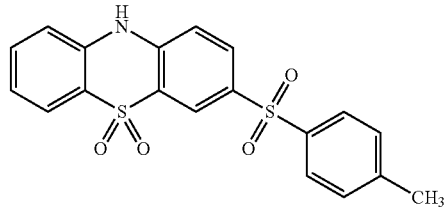

(18)

[Chemical Formula 11]

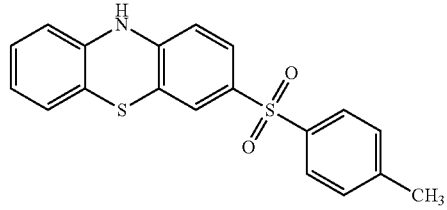

(19)

First, the following method was used to produce the intermediate A. That is, a two-necked reactor was charged with phenothiazine 13.34 g (66.94 mmol) and sodium p-toluenesulfinate 13.12 g (73.63 mmol), then these were made to dissolve in methanol 500 ml. Next, to this solution, potassium acetate 13.14 g (133.9 mmol) and iron trichloride 86.87 g (538.6 mmol) were added and the entire volume was made to react under refluxing conditions for 3 hours. After that, the reaction solution was concentrated by an evaporator down to 50 ml or so, then was charged with 0.2N hydrochloric acid aqueous solution 300 ml and saturated sodium chloride solution 500 ml and was extracted by ethyl acetate 800 ml. The extracted organic layer was further washed by 0.1N sodium hydroxide aqueous solution 200 ml, dried over anhydrous sodium sulfate, and concentrated by a rotary evaporator. The concentrate was made to dissolve in tetrahydrofuran (THF) and was reprecipitated by adding methanol to thereby obtain a white crystal intermediate A in 12.07 g (yield 51%). The structure of the obtained intermediate A was identified by $^1$H-NMR. $^1$H-NMR (500 MHz, DMSO-d6, TMS, δppm): 2.36 (s, 3H), 6.66 (d, 1H, J=7.5 Hz), 6.72 (d, 1H, J=8.5 Hz), 6.80 (t, 1H, J=7.5 Hz), 6.90 (d, 1H, J=7.5 Hz), 7.00 (t, 1H, J=7.5 Hz), 7.37 (d, 1H, J=1.5 Hz), 7.39 (d, 2H, J=8.0 Hz), 7.48 (dd, 1H, J=8.5, 1.5 Hz), 7.77 (d, 2H, J=8.0 Hz), 9.17 (s, 1H).

Next, the obtained intermediate A was used in accordance with the following method to obtain the compound 2. That is, first, a two-necked reactor was charged with the obtained intermediate A 11.0 g (31.12 mmol), then this was made to dissolve in THF 800 ml. Next, to this solution, acetic acid 600 ml and 30% hydrogen peroxide solution 21.17 g (186.7 mmol) were added and the total volume was made to react at 80° C. for 2 hours. The reaction solution was returned to room temperature, then was charged into distilled water 4 liters. The precipitated crystal was filtered. The obtained crystal was made to dissolve in THF and was made to reprecipitate by adding n-hexane to obtain a white crystal compound 2 in 11.05 g for a yield of 93%. The structure of the obtained compound 2 was identified by $^1$H-NMR. $^1$H-NMR (500 MHz, DMSO-d6, TMS, δppm): 2.37 (s, 3H), 7.36 (t, 1H, J=7.5 Hz), 7.41 (d, 1H, J=8.5 Hz), 7.44 (d, 2H, J=8.0 Hz), 7.51 (d, 1H, J=9.0 Hz), 7.73 (t, 1H, J=8.0 Hz), 7.84 (d, 2H, J=8.0 Hz), 7.99 (d, 1H, J=8.0 Hz), 8.12 (dd, 1H, J=9.0, 1.5 Hz), 8.34 (d, 1H, J=1.5 Hz), 11.53 (s, 1H).

Manufacturing Example 3

Synthesis of Compound 3

The following method was followed to synthesize the compound 3 of the following formula (20). Note that, when synthesizing the compound 3, this was synthesized by first obtaining the intermediate B which is shown by the following formula (21), next obtaining the intermediate C which is shown by the following formula (22) from the obtained intermediate B, and finally oxidizing the obtained intermediate C.

[Chemical Formula 12]

(20)

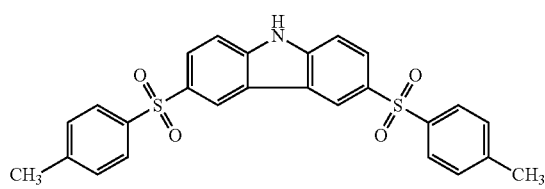

[Chemical Formula 13]

(21)

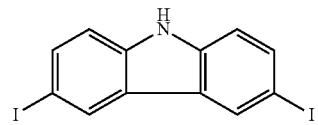

[Chemical Formula 14]

(22)

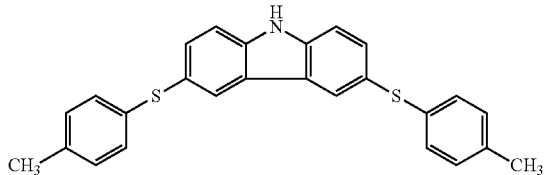

First, the following method was used to produce the intermediate B. That is, a two-necked reactor was charged with carbazole 25.0 g (149.5 mmol) and iodine 30.36 g (239.2 mmol), then these were made to dissolve in ethanol 600 ml. Next, to this solution, sodium periodate 12.8 g (59.80 mmol) was added, furthermore, concentrated sulfuric acid 1 g was slowly added dropwise, then the total volume was made to react at 65° C. for 3 hours. After that, the reaction solution was returned to room temperature and concentrated by a rotary evaporator down to 150 ml or so, then the concentrated solution was charged with distilled water 500 ml and saturated sodium chloride solution 300 ml and was extracted by chloroform 1000 ml. The organic layer was made to dry over anhydrous sodium sulfate, was concentrated by a rotary evaporator, then the concentrate was charged with n-hexane to recrystallize it so as to obtain the intermediate B in 34.4 g for a yield of 55%. The structure of the obtained intermediate B was identified by $^1$H-NMR. $^1$H-NMR (500 MHz, DMSO-d6, TMS, δppm): 7.35 (d, 2H, J=8.5 Hz), 7.66 (dd, 2H, J=8.5, 1.5 Hz), 8.57 (d, 2H, J=1.5 Hz), 11.54 (s, 1H).

Next, the obtained intermediate B was used in accordance with the following method to obtain the intermediate C. That is, first, a two-necked reactor was charged, under a flow of nitrogen, with the above obtained intermediate B 15.0 g (35.80 mmol) and p-toluenethiol 9.34 g (75.18 mmol), then these were made to dissolve in toluene 350 ml. Next, to this solution, sodium tert-butoxide 17.20 g (179.0 mmol) and [1,1'-bis(diphenylphosphino)ferrocene]palladium(II)dichloride dichloromethane adduct 0.73 g (0.895 mmol) were added and the total volume was made to react at 80° C. for 4 hours. After that, the reaction solution was returned to room temperature, was charged with distilled water 1000 ml and saturated sodium chloride solution 500 ml, and was extracted by ethyl acetate 500 ml. The organic layer was made to dry over anhydrous sodium sulfate, was concentrated by a rotary evaporator, then was purified by silica gel column chromatography (n-hexane:tetrahydrofuran=3:1 (volume ratio)) to obtain the intermediate C in 9.14 g for a yield of 62%. The structure of the obtained intermediate C was identified by $^1$H-NMR. $^1$H-NMR (500 MHz, CDCl$_3$, TMS, δppm): 2.29 (s, 6H), 7.05 (d, 4H, J=8.0 Hz), 7.15 (d, 4H, J=8.0 Hz), 7.37 (d, 2H, J=8.5 Hz), 7.51 (dd, 2H, J=8.5, 1.5 Hz), 8.12 (d, 2H, J=1.5 Hz), 8.18 (s, 1H).

Next, the obtained intermediate C was used in accordance with the following method to obtain the compound 3. That is, first, a two-necked reactor was charged with the intermediate C 8.00 g (19.44 mmol), then this was made to dissolve in THF 160 ml. Next, to this solution, acetic acid 240 ml and 30% hydrogen peroxide solution 13.22 g (116.6 mmol) were added and the total volume was made to react at 80° C. for 10 hours. The reaction solution was returned to room temperature, then was charged into distilled water 1.5 liters. The precipitated crystal was filtered, made to dissolve in THF, and reprecipitated by adding methanol to thereby obtain a white crystal compound 3 in 8.04 g for a yield of 87%. The structure of the obtained compound 3 was identified by $^1$H-NMR. $^1$H-NMR (500 MHz, DMSO-d6, TMS, δppm): 2.34 (s, 6H), 7.40 (d, 4H, J=8.0 Hz), 7.71 (d, 2H, J=8.5 Hz), 7.89 (d, 4H, J=8.0 Hz), 7.99 (dd, 2H, J=8.5, 1.5 Hz), 9.11 (d, 2H, J=1.5 Hz), 12.33 (s, 1H).

The chemical structures and molecular weights of the compounds 1 to 3 which were synthesized by the above manufacturing examples and 4,4'-bis(α,α-dimethylbenzyl)diphenylamine, N,N'-di-2-naphthyl-p-phenylenediamine, 2,2'-methylene bis(4-methyl-6-t-butylphenol), 2,6-di-t-butyl-4-methylphenol, 2-mercaptobenzimidazole, and tris(nonylphenyl)phosphate which were used in the comparative examples and have been used in the past as antiaging agents are shown together in Table 1.

TABLE 1

| | Chemical structure | Molecular weight |
|---|---|---|
| Compound 1 | 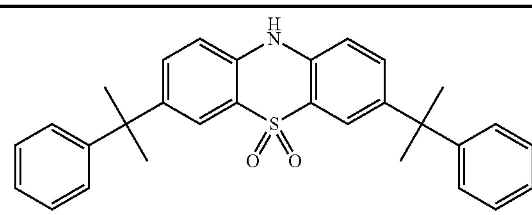 | 467.6 |
| Compound 2 | 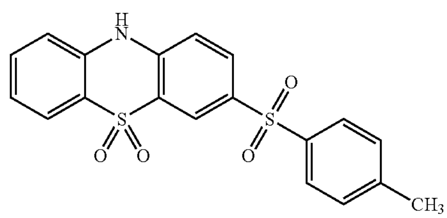 [SMILES: Cc1ccc(S(=O)(=O)c2ccc3c(c2)S(=O)(=O)c2ccccc2N3)cc1] | 385.5 |
| Compound 3 | 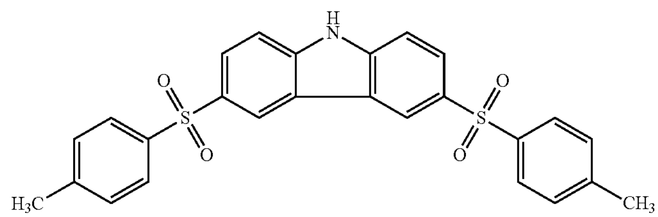 | 475.6 |
| 4,4'-bis (α,α-dimethylbenzyl) diphenylamine | 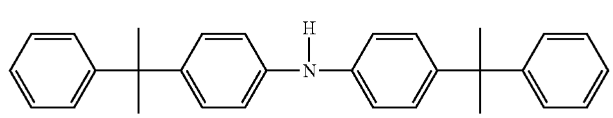 [SMILES: CC(C)(c1ccccc1)c1ccc(Nc2ccc(C(C)(C)c3ccccc3)cc2)cc1] | 405.6 |
| N,N'-di-2-naphthyl-p-phenylene diamine | 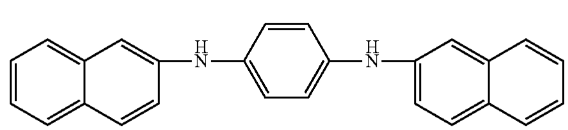 [SMILES: c1ccc2cc(Nc3ccc(Nc4ccc5ccccc5c4)cc3)ccc2c1] | 360.5 |
| 2,2'-methylene-bis(4-methyl-6-t-butyl-phenol) | 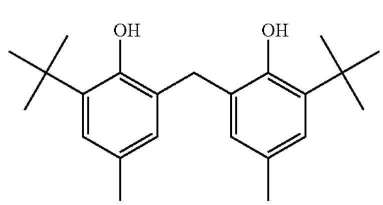 [SMILES: Cc1cc(Cc2cc(C)cc(C(C)(C)C)c2O)c(O)c(C(C)(C)C)c1] | 340.5 |

TABLE 1-continued

| Chemical structure | Molecular weight |
|---|---|
| 2,6-di-t-butyl-4-methylphenol | 220.35 |
| 2-mercaptobenzimidazole | 150.2 |
| Tris(nonylphenyl) phosphite | 737.1 |

(Manufacturing Example 1 of Acrylic Rubber)

A polymerization reactor equipped with a thermometer and a stirring device was charged with water 200 parts, sodium lauryl sulfate 3 parts, ethyl acrylate 58 parts, n-butyl acrylate 40 parts, and mono n-butyl fumarate 2 parts. After that, the reactor was deaerated under reduced pressure and substituted by nitrogen two times to fully remove the oxygen, then was charged with cumen hydroperoxide 0.005 part and sodium formaldehyde sulfoxylate 0.002 part to start the emulsion polymerization under ordinary pressure at a temperature of 30° C. The reaction was continued until the polymerization conversion reached 95%. The obtained emulsion polymerization solution was coagulated by a calcium chloride aqueous solution, then rinsed and dried to obtain a carboxyl group-containing acrylic rubber A. The obtained carboxyl group-containing acrylic rubber A had a Mooney viscosity ($ML_{1+4}$, 100° C.) of 45. Note that, the composition of the obtained carboxyl group-containing acrylic rubber A was 58 wt % of ethyl acrylate units, 40 wt % of n-butyl acrylate units, and 2 wt % of mono n-butyl fumarate units.

(Manufacturing Example 2 of Acrylic Rubber)

A polymerization reactor equipped with a thermometer and a stirring device was charged with water 200 parts, sodium lauryl sulfate 3 parts, ethyl acrylate 49 parts, n-butyl acrylate 49 parts, and mono n-butyl fumarate 2 parts. After that, the reactor was deaerated under reduced pressure and substituted by nitrogen two times to fully remove the oxygen, then was charged with cumen hydroperoxide 0.005 part and sodium formaldehyde sulfoxylate 0.002 part to start the emulsion polymerization under ordinary pressure at a temperature of 30° C. The reaction was continued until the polymerization conversion reached 95%. The obtained emulsion polymerization solution was coagulated by a calcium chloride aqueous solution, then rinsed and dried to obtain a carboxyl group-containing acrylic rubber B. The obtained carboxyl group-containing acrylic rubber B had a Mooney viscosity ($ML_{1+4}$, 100° C.) of 35. Note that, the composition of the obtained carboxyl group-containing acrylic rubber B was 49 wt % of ethyl acrylate units, 49 wt % of n-butyl acrylate units, and 2 wt % of mono n-butyl fumarate units.

(Manufacturing Example 3 of Acrylic Rubber)

A polymerization reactor equipped with a thermometer and a stirring device was charged with water 200 parts, sodium lauryl sulfate 3 parts, ethyl acrylate 98.0 parts, methacrylic acid 0.5 part, and p-chloromethylstyrene 1.5 parts. After that, the reactor was deaerated under reduced pressure and substituted by nitrogen two times to fully remove the oxygen, then was charged with cumen hydroperoxide 0.005 part and sodium formaldehyde sulfoxylate 0.002 part to start the emulsion polymerization under ordinary pressure at a temperature of 30° C. The reaction was continued until the polymerization conversion reached 95%. The obtained emulsion polymerization solution was coagulated by a calcium chloride aqueous solution, then rinsed and dried to obtain a carboxyl group- and chlorine atom-containing acrylic rubber C. The obtained carboxyl group- and chlorine atom-containing acrylic rubber C had a Mooney viscosity ($ML_{1+4}$, 100° C.) of 50. Note that, the composition of the obtained carboxyl group- and chlorine atom-containing acrylic rubber C was 98.0 wt % of ethyl acrylate units, 0.5 wt % of methacrylic acid units, and 1.5 wt % of p-chloromethylstyrene units.

Methods of Evaluation of Examples 1-1 to 1-8 and Comparative Examples 1-1 to 1-4

The various tests of the physical properties in Examples 1-1 to 1-8 and Comparative Examples 1-1 to 1-4 were performed by the following methods.

(Test of Original Properties)

The acrylic rubber composition was shaped by a press and cross-linked at 170° C. by 10 MPa for 20 minutes to obtain a 15 cm×15 cm×2 mm sheet. This was heated at 170° C. for 4 hours to cause secondary cross-linking. From the secondary cross-linked sheet, a dumbbell shaped No. 3 test piece was prepared. Further, the obtained test piece was used to measure the tensile strength (strength), the elongation at break (elongation), and the modulus at 100% as mechanical properties under ordinary temperature in accordance with the tensile test of JIS K6251. Further, the hardness was measured in accordance with the hardness test of JIS K6253.

(Heat Resistance Test)<
<Heat Resistance Test for Applications of Extruded Products>

The heat resistance test was performed by heating a test piece, which was prepared in the same way as the test of original properties, in a 180° C. environment for 1000 hours to cause heat aging and by using that piece.

Specifically, first, the elongations before and after heating were measured in accordance with JIS K6251, then the following formula was used to calculate the rate of change to thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

Further, the test piece after heat aging was used to measure the modulus at 100% in accordance with JIS K6251. A test piece which ended up being torn in the middle of the test was evaluated as "BO" (bending out).

Furthermore, as a bending test, the test piece after heat aging was bent 180° and evaluated in appearance for occurrence of cracks, breaks, or other abnormalities. Test pieces free of cracks, breaks, and other abnormalities were evaluated as "Good", while test pieces which suffered from cracks, breaks, or other abnormalities were evaluated as "Poor".

<Heat Resistance Test for Applications of Seal Members>

The acrylic rubber composition was shaped by a press and cross-linked at 170° C. by 10 MPa for 20 minutes to prepare a columnar test piece of a diameter of 29 mm and thickness of 12.5 mm. This was further heated at 170° C. for 4 hours to cause secondary cross-linking. Further, the test piece after secondary cross-linking was measured for the rate of compression set in accordance with JIS K6262 by pressing the test piece by 25%, allowing it to stand in that state in a 180° C. environment for 168 hours, then releasing the pressure.

Example 1-1

The carboxyl group-containing acrylic rubber A, which was obtained by the above-mentioned Manufacturing Example 1 of acrylic rubber, 100 parts by weight, carbon black (made by Tokai Carbon, Seast SO) 60 parts by weight, stearic acid 2 parts by weight, and the compound 1 (antiaging agent), which was obtained by the above-mentioned Manufacturing Example 1, 2.30 parts by weight (with respect to rubber 100 g, 4.93 mmol) were kneaded using a 0.8 liter Bambury mixer at 50° C. for 5 minutes, then a cross-linking agent constituted by 2,2-bis[4-(4-amino phenoxy)phenyl] propane (made by Wakayama Seika Kogyo, BAPP) 1 part by weight and a cross-linking accelerator constituted by dialkyl ($C_8$ to $C_{18}$)amine (made by Lion Akzo, Armeen 2C) 2 parts by weight were added and the result kneaded by open roll at 50° C. to prepare an acrylic rubber composition. Further, the obtained acrylic rubber composition was used in accordance with the above methods to perform a test on the original properties and heat resistance test for applications of extruded products such as the rate of change of elongation, modulus at 100%, and bending test. The results are shown in Table 2.

Example 1-2

Except for changing the amount of the compound 1 (antiaging agent) to 5.95 parts (with respect to rubber 100 g, 12.73 mmol), the same procedure was followed as in Example 1-1 to obtain an acrylic rubber composition and similarly evaluate it. The results are shown in Table 2.

Examples 1-3, 1-4 and Comparative Examples 1-1, 1-2

Except for using, instead of the compound 1 (antiaging agent), the compound 2 (antiaging agent) which was obtained in the above-mentioned Manufacturing Example 2 (Example 1-3), the compound 3 (antiaging agent) which was obtained in the above-mentioned Manufacturing Example 3 (Example 1-4), and 4,4'-bis(α,α-dimethylbenzyl)diphenylamine (antiaging agent, made by Chemtura Nauguard 445) (Comparative Examples 1-1 and 1-2) and making the amounts of these the amounts which are shown in Table 2, the same procedure was followed as in Example 1-1 to obtain acrylic rubber compositions and similarly evaluate them. The results are shown in Table 2.

TABLE 2

| Formulation | | Ex. 1-1 | Ex. 1-2 | Ex. 1-3 | Ex. 1-4 | Comp. Ex. 1-1 | Comp. Ex. 1-2 |
|---|---|---|---|---|---|---|---|
| Carboxyl group-containing acrylic rubber A | Parts by weight | 100 | 100 | 100 | 100 | 100 | 100 |
| Carbon black | Parts by weight | 60 | 60 | 60 | 60 | 60 | 60 |
| Stearic acid | Parts by weight | 2 | 2 | 2 | 2 | 2 | 2 |
| Antiaging agent Type | | Compound 1 | Compound 1 | Compound 2 | Compound 3 | 4,4'-bis(α,α-dimethylbenzyl)-diphenylamine | 4,4'-bis(α,α-dimethylbenzyl)-diphenylamine |
| Amount of addition to rubber 100 parts by weight | Parts by weight | 2.30 | 5.95 | 4.91 | 6.05 | 2.00 | 5.16 |
| Amount of addition to rubber 100 g | mmol | 4.93 | 12.73 | 12.73 | 12.73 | 4.93 | 12.73 |
| 2,2-bis[4-(4-aminophenoxy)phenyl]propane | Parts by weight | 1 | 1 | 1 | 1 | 1 | 1 |
| Dialkyl($C_8$ to $C_{18}$)amine | Parts by weight | 2 | 2 | 2 | 2 | 2 | 2 |
| Original properties | Tensile strength [MPa] | 10.2 | 9.9 | 10.5 | 10.6 | 9.8 | 9.4 |
| | Elongation [%] | 250 | 260 | 270 | 230 | 260 | 280 |
| | 100% modulus [MPa] | 3.3 | 3.1 | 4.2 | 4.0 | 4.1 | 4.0 |
| | Hardness [Duro A] | 61 | 61 | 65 | 64 | 64 | 63 |

TABLE 2-continued

| | Formulation | | Ex. 1-1 | Ex. 1-2 | Ex. 1-3 | Ex. 1-4 | Comp. Ex. 1-1 | Comp. Ex. 1-2 |
|---|---|---|---|---|---|---|---|---|
| Heat resistance test for applications of extruded products | Rate of change of elongation [%] After 180° C. 1000 hours | | −64 | −62 | −70 | −72 | −80 | −79 |
| | 100% modulus [MPa] After 180° C. 1000 hours | | 3.9 | 3.6 | 4.9 | 4.8 | BO | BO |
| | Bending test After 180° C. 1000 hours | | Good | Good | Good | Good | Poor | Poor |

BO: Bending out

Evaluation of Examples 1-1 to 1-4 and Comparative Examples 1-1, 1-2

As shown in Table 2, in Examples 1-1 to 1-4 which used antiaging agents constituted by predetermined compounds of the present invention (compounds 1 to 3), even after going through severe conditions of an environment of 180° C. for 1000 hours, compared with Comparative Examples 1-1 and 1-2, the rates of change of elongation were close to 0 and the changes of elongation were small. Further, in the modulus at 100% as well, while Comparative Examples 1-1 and 1-2 resulted in bending out (BO), in Examples 1-1 to 1-4, the test piece were not torn. Furthermore, in the bending test, while Comparative Examples 1-1 and 1-2 ended up breaking in the middle, in Examples 1-1 to 1-4, even if bent 180°, no cracks occurred and no breakage happened. It was confirmed that the cross-linked rubber products obtained by using the acrylic rubber compositions of the present invention were improved in heat resistance in the heat resistance test for applications for extruded products.

Example 1-5

The carboxyl group-containing acrylic rubber B, which was obtained by the above-mentioned Manufacturing Example 2 of acrylic rubber, 100 parts by weight, carbon black (made by Tokai Carbon, Seast SO) 60 parts by weight, stearic acid 2 parts by weight, and the compound 1 (antiaging agent), which was obtained by the above-mentioned Manufacturing Example 1, 2.30 parts by weight (with respect to rubber 100 g, 4.93 mmol) were kneaded using a 0.8 liter Bambury mixer at 50° C. for 5 minutes, then a cross-linking agent constituted by hexamethylenediamine carbamate (made by Dupont Dow Elastomer Japan, Diak No. 1) 0.6 part by weight and a cross-linking accelerator constituted by 1,3-di-o-tolylguanidine (made by Ouchi Shinko Chemical Industrial, Nocceler DT) 2 parts by weight were added and the result kneaded by open roll at 50° C. to prepare an acrylic rubber composition. Further, the obtained acrylic rubber composition was used in accordance with the above methods to perform a test on the original properties and a heat resistance test for applications of seal members constituted by measurement of the rate of compression set. The results are shown in Table 3.

Example 1-6

Except for changing the amount of the compound 1 (antiaging agent) to 5.95 parts (with respect to rubber 100 g, 12.73 mmol), the same procedure was followed as in Example 1-5 to obtain an acrylic rubber composition and similarly evaluate it. The results are shown in Table 3.

Examples 1-7, 1-8 and Comparative Examples 1-3, 1-4

Except for using, instead of the compound 1 (antiaging agent), the compound 2 (antiaging agent) which was obtained by the above-mentioned Manufacturing Example 2 (Example 1-7), the compound 3 (antiaging agent) which was obtained by the above-mentioned Manufacturing Example 3 (Example 1-8), and 4,4'-bis($\alpha,\alpha$-dimethylbenzyl)diphenylamine (antiaging agent, made by Chemtura Nauguard 445) (Comparative Examples 1-3 and 1-4) and making the amounts of these the amounts which are shown in Table 3, the same procedures were followed as in Example 1-5 to obtain acrylic rubber compositions and similarly evaluate them. The results are shown in Table 3.

TABLE 3

| | Formulation | | Ex. 1-5 | Ex. 1-6 | Ex. 1-7 | Ex. 1-8 | Comp. Ex. 1-3 | Comp. Ex. 1-4 |
|---|---|---|---|---|---|---|---|---|
| | Carboxyl group-containing acrylic rubber B | Parts by weight | 100 | 100 | 100 | 100 | 100 | 100 |
| | Carbon black | Parts by weight | 60 | 60 | 60 | 60 | 60 | 60 |
| | Stearic acid | Parts by weight | 2 | 2 | 2 | 2 | 2 | 2 |
| Antiaging agent | Type | | Compound 1 | Compound 1 | Compound 2 | Compound 3 | 4,4'-bis($\alpha,\alpha$-dimethylbenzyl)-diphenylamine | |
| | Amount of addition to rubber 100 parts by weight | Parts by weight | 2.30 | 5.95 | 4.91 | 6.05 | 2.00 | 5.16 |
| | Amount of addition to rubber 100 g | mmol | 4.93 | 12.73 | 12.73 | 12.73 | 4.93 | 12.73 |
| | Hexamethylene diamine carbamate | Parts by weight | 0.6 | 0.6 | 0.6 | 0.6 | 0.6 | 0.6 |
| | 1,3-di-o-tolylguanidine | Parts by weight | 2 | 2 | 2 | 2 | 2 | 2 |
| | Original properties | Tensile strength [MPa] | 10.3 | 10.0 | 10.4 | 10.6 | 9.9 | 9.3 |
| | | Elongation [%] | 250 | 260 | 260 | 240 | 250 | 270 |
| | | Hardness [Duro A] | 62 | 61 | 66 | 65 | 64 | 63 |
| Heat resistance test for applications of seal members | Rate of compression set [%] After 180° C. 168 hours | | 18 | 17 | 19 | 20 | 23 | 24 |

Evaluation of Examples 1-5 to 1-8 and Comparative Examples 1-3, 1-4

As shown in Table 3, in Examples 1-5 to 1-8 which used antiaging agents constituted by predetermined compounds of the present invention (compounds 1 to 3), even after going through severe conditions of an environment of 180° C. for 168 hours, compared with Comparative Examples 1-3 and 1-4, the rates of compression set were small. It was confirmed that the cross-linked rubber products obtained by using the acrylic rubber compositions of the present invention were improved in heat resistance in the heat resistance test for applications for seal members as well.

Methods of Evaluation of Examples 2-1 to 2-9 and Comparative Examples 2-1 to 2-4

The various tests of the physical properties in Examples 2-1 to 2-9 and Comparative Examples 2-1 to 2-4 were performed by the following methods.
(Test of Original Properties)
The same procedures were performed as in Examples 1-1 to 1-8 and Comparative Examples 1-1 to 1-4 to obtain test pieces and measure the tensile strength (strength), elongation at break (elongation), and hardness.
(Heat Resistance Test)
The heat resistance test was performed by heating a test piece, which was prepared in the same way as the test of original properties, in a 190° C. environment for 500 hours to cause heat aging and by using that piece. Specifically, first, the elongations before and after heating were measured in accordance with JIS K6251, then the following formula was used to calculate the rate of change to thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

Further, the tensile strengths before and after heating were measured in accordance with the tensile test of JIS K6251, then the following formula was used to calculate the rate of change to thereby measure the rate of change of strength. The closer the rate of change of strength to zero, the higher the heat resistance is judged and the more preferable the result.

Rate of change of strength (%)=100×[(tensile strength after heating (MPa))−(tensile strength before heating (MPa))]/(tensile strength before heating (MPa))

Example 2-1

The carboxyl group-containing acrylic rubber A, which was obtained by the above-mentioned Manufacturing Example 1 of acrylic rubber, 100 parts by weight, carbon black (made by Tokai Carbon, Seast SO) 60 parts by weight, stearic acid 2 parts by weight, and the compound 1 (antiaging agent), which was obtained by the above-mentioned Manufacturing Example 1, 0.50 part by weight were kneaded using a 0.8 liter Bambury mixer at 50° C. for 5 minutes, then a cross-linking agent constituted by 2,2-bis[4-(4-amino phenoxy)phenyl]propane (made by Wakayama Seika Kogyo, BAPP) 1 part by weight and a cross-linking accelerator constituted by dialkyl($C_8$ to $C_{18}$)amine (made by Lion Akzo, Armeen 2C) 2 parts by weight were added and the result kneaded by open roll at 50° C. to prepare an acrylic rubber composition. Further, the obtained acrylic rubber composition was used in accordance with the above methods to perform a test on the original properties and heat resistance test constituted by measurement of the rate of change of elongation and rate of change of strength. The results are shown in Table 4.

Examples 2-2 to 2-5

Except for changing the amounts of the compound 1 (antiaging agent) to 0.75 part (Example 2-2), 1.00 part (Example 2-3), 2.00 parts (Example 2-4), and 4.00 parts (Example 2-5), the same procedures were followed as in Example 2-1 to obtain acrylic rubber compositions and similarly evaluate them. The results are shown in Table 4.

Comparative Examples 2-1 to 2-3

Except for using, instead of the compound 1 (antiaging agent), 4,4'-bis(α,α-dimethylbenzyl)diphenylamine (antiaging agent, made by Chemtura, Nauguard 445) and making the amounts 1.00 part (Comparative Example 2-1), 2.00 parts (Comparative Example 2-2), and 4.00 parts (Comparative Example 2-3), the same procedures were followed as in Example 2-1 to obtain acrylic rubber compositions and similarly evaluate them. The results are shown in Table 4.

TABLE 4

| Formulation | | Ex. 2-1 | Ex. 2-2 | Ex. 2-3 | Ex. 2-4 | Ex. 2-5 | Comp. Ex. 2-1 | Comp. Ex. 2-2 | Comp. Ex. 2-3 |
|---|---|---|---|---|---|---|---|---|---|
| Carboxyl group-containing acrylic rubber A | Parts by weight | 100 | 100 | 100 | 100 | 100 | 100 | 100 | 100 |
| Carbon black | Parts by weight | 60 | 60 | 60 | 60 | 60 | 60 | 60 | 60 |
| Stearic acid | Parts by weight | 2 | 2 | 2 | 2 | 2 | 2 | 2 | 2 |
| Antiaging agent Type | | Compound 1 | | | | | 4,4'-bis(α,α-dimethylbenzyl)diphenylamine | | |
| Amount of addition to rubber 100 parts by weight | Parts by weight | 0.50 | 0.75 | 1.00 | 2.00 | 4.00 | 1.00 | 2.00 | 4.00 |
| 2,2-bis[4-(4-aminophenoxy)phenyl]propane | Parts by weight | 1 | 1 | 1 | 1 | 1 | 1 | 1 | 1 |
| Dialkyl($C_8$ to $C_{18}$)amine | Parts by weight | 2 | 2 | 2 | 2 | 2 | 2 | 2 | 2 |
| Original properties | Tensile strength [MPa] | 10.1 | 10.1 | 9.8 | 9.8 | 9.5 | 10.2 | 10.1 | 9.7 |
| | Elongation [%] | 250 | 250 | 260 | 250 | 250 | 250 | 260 | 260 |
| | Hardness [Duro A] | 64 | 63 | 64 | 63 | 62 | 63 | 64 | 62 |

TABLE 4-continued

| Formulation | | Ex. 2-1 | Ex. 2-2 | Ex. 2-3 | Ex. 2-4 | Ex. 2-5 | Comp. Ex. 2-1 | Comp. Ex. 2-2 | Comp. Ex. 2-3 |
|---|---|---|---|---|---|---|---|---|---|
| Heat resistance test | Rate of change of strength [%] After 190° C. 500 hours | −31 | −32 | −38 | −55 | −62 | −46 | −50 | −56 |
| | Rate of change of elongation [%] After 190° C. 500 hours | −68 | −64 | −58 | −60 | −64 | −77 | −73 | −71 |

Evaluation of Examples 2-1 to 2-5 and Comparative Examples 2-1 to 2-3

As shown in Table 4, in Examples 2-1 to 2-5 which used antiaging agents constituted by predetermined compound 1 of the present invention, even after going through severe conditions of an environment of 190° C. for 500 hours, compared with Comparative Examples 2-1 and 2-3, the rates of change of elongation were close to 0 and the changes of elongation were small. Further, in the rates of change of strength as well, the absolute values were smaller than 70%. Even after being exposed long term to high temperature conditions, certain levels or more of strength were maintained. Accordingly, it was confirmed that the cross-linked rubber products obtained by using the acrylic rubber compositions of the present invention were superior in balance of physical properties of elongation and strength in the heat resistance tests and were improved in heat resistance. Note that, the cross-linked rubber products of Comparative Examples 2-1 to 2-3 were inferior in heat resistance, so it is considered that degradation by hardening occurs more due to being exposed long term to high temperature conditions. In terms of numerical values, certain levels or more strength were maintained.

Example 2-6

The carboxyl group-containing acrylic rubber B, which was obtained by the above-mentioned Manufacturing Example 2 of acrylic rubber, 100 parts by weight, carbon black (made by Tokai Carbon, Seast SO) 60 parts by weight, stearic acid 2 parts by weight, and the compound 1 (antiaging agent), which was obtained by the above-mentioned Manufacturing Example 1 of the compound, 0.50 part by weight were kneaded using a 0.8 liter Bambury mixer at 50° C. for 5 minutes, then a cross-linking agent constituted by hexamethylenediamine carbamate (made by Dupont Dow Elastomer Japan, Diak No. 1) 0.6 part by weight and a cross-linking accelerator constituted by 1,3-di-o-tolylguanidine (made by Ouchi Shinko Chemical Industrial, Nocceler DT) 2 parts by weight were added and the result kneaded by open roll at 50° C. to prepare an acrylic rubber composition. Further, the obtained acrylic rubber composition was used in accordance with the above methods to perform a test on the original properties and heat resistance test constituted by measurement of the rate of change of elongation and rate of change of strength. The results are shown in Table 5.

Examples 2-7 to 2-9

Except for changing the amounts of the compound 1 (antiaging agent) to 1.00 part (Example 2-7), 2.00 parts (Example 2-8), and 4.00 parts (Example 2-9), the same procedures were followed as in Example 2-6 to obtain acrylic rubber compositions and similarly evaluate them. The results are shown in Table 5.

Comparative Example 2-4

Except for using, instead of the compound 1 (antiaging agent), 4,4'-bis(α,α-dimethylbenzyl)diphenylamine (antiaging agent, made by Chemtura, Nauguard 445) and making the amount 2.00 parts, the same procedure was followed as in Example 2-6 to obtain an acrylic rubber composition and similarly evaluate it. The results are shown in Table 5.

TABLE 5

| Formulation | | Ex. 2-6 | Ex. 2-7 | Ex. 2-8 | Ex. 2-9 | Comp. Ex. 2-4 |
|---|---|---|---|---|---|---|
| Carboxyl group-containing acrylic rubber B | Parts by weight | 100 | 100 | 100 | 100 | 100 |
| Carbon black | Parts by weight | 60 | 60 | 60 | 60 | 60 |
| Stearic acid | Parts by weight | 2 | 2 | 2 | 2 | 2 |
| Antiaging agent | Type | Compound 1 | | | | 4,4'-bis(α,α-dimethylbenzyl)diphenylamine |
| Amount of addition to rubber 100 parts by weight | Parts by weight | 0.50 | 1.00 | 2.00 | 4.00 | 2.00 |
| Hexamethylene diamine carbamate | Parts by weight | 0.6 | 0.6 | 0.6 | 0.6 | 0.6 |
| 1,3-di-o-tolylguanidine | Parts by weight | 2 | 2 | 2 | 2 | 2 |
| Original properties | Tensile strength [MPa] | 10.6 | 10.4 | 10.5 | 10.2 | 10.2 |
| | Elongation [%] | 240 | 230 | 240 | 230 | 250 |
| | Hardness [Duro A] | 65 | 64 | 63 | 63 | 65 |
| Heat resistance test | Rate of change of strength [%] After 190° C. 500 hours | −36 | −41 | −54 | −60 | −47 |
| | Rate of change of elongation [%] After 190° C. 500 hours | −69 | −60 | −61 | −64 | −73 |

Evaluation of Examples 2-6 to 2-9 and Comparative Example 2-4

As shown in Table 5, in Examples 2-6 to 2-9 which used antiaging agents constituted by predetermined compound 1 of the present invention, even after going through severe conditions of an environment of 190° C. for 500 hours, compared with Comparative Example 2-4, the rates of change of elongation were close to 0 and the changes of elongation were small. Further, in the rates of change of strength as well, the absolute values were smaller than 70%. Even after being exposed long term to high temperature conditions, certain levels or more of strength were maintained. Accordingly, it was confirmed that the cross-linked rubber products obtained by using the acrylic rubber compositions of the present invention were superior in balance of physical properties of elongation and strength in the heat resistance tests and were improved in heat resistance regardless of the types of the cross-linking agents and cross-linking accelerators.

Methods of Evaluation of Examples 3-1 to 3-4 and Comparative Examples 3-1, 3-2

The various tests of the physical properties in Examples 3-1 to 3-4 and Comparative Examples 3-1, 3-2 were performed by the following methods.

(Test of Original Properties)

The same procedures were performed as in Examples 1-1 to 1-8 and Comparative Examples 1-1 to 1-4 to obtain test pieces and measure the tensile strength (strength), elongation at break (elongation), modulus at 100%, and hardness.

(Heat Resistance Test)

The heat resistance test was performed by heating a test piece, which was prepared in the same way as the test of original properties, in a 175° C. environment for 500 hours or 1000 hours to cause heat aging and by using that piece. Specifically, first, the elongations before and after heating were measured in accordance with JIS K6251, then the following formula was used to calculate the rate of change to thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

Example 3-1

Epoxy group-containing acrylic rubber (made by Zeon Corporation, Nipol AR51) 100 parts by weight, carbon black (made by Tokai Carbon, Seast SO) 50 parts by weight, stearic acid 2 parts by weight, and the compound 1 (antiaging agent), which was obtained by above-mentioned Manufacturing Example 1, 1.00 part by weight were kneaded using a 0.8 liter Bambury mixer at 50° C. for 5 minutes, then a cross-linking agent constituted by zinc dimethyldithiocarbamate (made by Ouchi Shinko Chemical Industrial, Nocceler PZ) 2.5 part by weight, a cross-linking accelerator constituted by ferric dimethyldithiocarbamate (made by Ouchi Shinko Chemical Industrial, Nocceler TTEF) 0.5 part by weight and a scorch preventer constituted by a sulfonamide derivative (made by Lanxess, Vulkalent E/C) 0.5 part by weight were added, then the mixture was kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 6.

Example 3-2

Except for changing the amount of the compound 1 (antiaging agent) to 2.00 parts, the same procedure was followed as in Example 3-1 to obtain an acrylic rubber composition and similarly evaluate it. The results are shown in Table 6.

Example 3-3

Epoxy group-containing acrylic rubber (made by Zeon Corporation, Nipol AR51) 100 parts by weight, carbon black (made by Tokai Carbon, Seast SO) 50 parts by weight, stearic acid 2 parts by weight, and the compound 1 (antiaging agent), which was obtained by above-mentioned Manufacturing Example 1, 1.00 part by weight were kneaded using a 0.8 liter Bambury mixer at 50° C. for 5 minutes, then a cross-linking agent constituted by ammonium benzoate (made by Ouchi Shinko Chemical Industrial, Vulnoc AB-S) 1.5 parts by weight was added, then the mixture was kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 6.

Example 3-4

Except for changing the amount of the compound 1 (antiaging agent) to 2.00 parts, the same procedure was followed as in Example 3-3 to obtain an acrylic rubber composition and similarly evaluate it. The results are shown in Table 6.

Comparative Example 3-1

Except for using, instead of the compound 1 (antiaging agent), 4,4'-bis(α,α-dimethylbenzyl)diphenylamine (antiaging agent, made by Chemtura, Nauguard 445) and making the amount 2.00 parts, the same procedure was followed as in Example 3-1 to obtain an acrylic rubber composition and similarly evaluate it. The results are shown in Table 6.

Comparative Example 3-2

Except for using, instead of the compound 1 (antiaging agent), 4,4'-bis(α,α-dimethylbenzyl)diphenylamine(antiaging agent, made by Chemtura, Nauguard 445) and making the amount 2.00 parts, the same procedure was followed as in Example 3-3 to obtain an acrylic rubber composition and similarly evaluate it. The results are shown in Table 6.

TABLE 6

| Formulation | | | Ex. 3-1 | Ex. 3-2 | Ex. 3-3 | Ex. 3-4 | Comp. Ex. 3-1 | Comp. Ex. 3-2 |
|---|---|---|---|---|---|---|---|---|
| Epoxy group-containing acrylic rubber (Nipol AR51) | | Parts by weight | 100 | 100 | 100 | 100 | 100 | 100 |
| | Carbon black | Parts by weight | 50 | 50 | 50 | 50 | 50 | 50 |
| | Stearic acid | Parts by weight | 2 | 2 | 2 | 2 | 2 | 2 |
| Antiaging agent | | Type | Compound 1 | | | | 4,4'-bis(α,α-dimethylbenzyl)-diphenylamine | |

TABLE 6-continued

| Formulation | | Ex. 3-1 | Ex. 3-2 | Ex. 3-3 | Ex. 3-4 | Comp. Ex. 3-1 | Comp. Ex. 3-2 |
|---|---|---|---|---|---|---|---|
| Amount of addition to rubber 100 parts by weight | Parts by weight | 1.00 | 2.00 | 1.00 | 2.00 | 2.00 | 2.00 |
| Zinc dimethyldithiocarbamate | Parts by weight | 2.5 | 2.5 | — | — | 2.5 | — |
| Ferric dimethyldithiocarbamate | Parts by weight | 0.5 | 0.5 | — | — | 0.5 | — |
| Sulfonamide derivative | Parts by weight | 0.5 | 0.5 | — | — | 0.5 | — |
| Ammonium benzoate | Parts by weight | — | — | 1.5 | 1.5 | — | 1.5 |
| Original properties | Tensile strength [MPa] | 12.0 | 11.8 | 13.8 | 13.8 | 11.6 | 13.1 |
| | Elongation [%] | 490 | 490 | 320 | 340 | 520 | 350 |
| | 100% modulus [MPa] | 2.9 | 2.7 | 4.1 | 3.8 | 2.7 | 3.7 |
| | Hardness [Duro A] | 74 | 74 | 72 | 73 | 72 | 72 |
| Heat resistance test | Rate of change of elongation [%] After 175° C. 500 hours | −78 | −63 | — | — | −87 | — |
| | Rate of change of elongation [%] After 175° C. 1000 hours | — | — | −66 | −68 | — | −83 |

Evaluation of Examples 3-1 to 3-4 and Comparative Examples 3-1, 3-2

As shown in Table 6, in Examples 3-1 to 3-4 which used antiaging agents constituted by predetermined compound 1 of the present invention, even after going through severe conditions of an environment of 175° C. for 500 hours or 1000 hours, compared with Comparative Examples 3-1 and 3-2, the rates of change of elongation were close to 0 and the changes in elongation were small. Accordingly, it was confirmed that the cross-linked rubber products which were obtained by using the acrylic rubber compositions of the present invention were improved in heat resistance in the heat resistance test regardless of the type of the cross-linking agents.

Methods of Evaluation of Examples 4-1 to 4-4 and Comparative Examples 4-1, 4-2

The various tests of the physical properties in Examples 4-1 to 4-4 and Comparative Examples 4-1, 4-2 were performed by the following methods.

(Test of Original Properties)

The same procedures were performed as in Examples 1-1 to 1-8 and Comparative Examples 1-1 to 1-4 to obtain test pieces and measure the tensile strength (strength), elongation at break (elongation), modulus at 100%, and hardness.

(Heat Resistance Test)

The heat resistance test was performed by heating a test piece, which was prepared in the same way as the test of original properties, in a 190° C. environment for 500 hours to cause heat aging and by using that piece. Specifically, first, the elongations before and after heating were measured in accordance with JIS K6251, then the following formula was used to calculate the rate of change to thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

Example 4-1

Chlorine atom-containing acrylic rubber (made by Zeon Corporation, Nipol AR71) 100 parts by weight, carbon black (made by Tokai Carbon, Seast SO) 50 parts by weight, stearic acid 2 parts by weight, and the compound 1 (antiaging agent), which was obtained by the above-mentioned Manufacturing Example 1, 1.00 parts by weight were kneaded using a 0.8 liter Bambury mixer at 50° C. for 5 minutes, then a cross-linking agent constituted by sulfur (made by Tsurumi Chemical Industry, Sulfax PMC) 0.3 part by weight and cross-linking accelerators constituted by sodium stearate (made by Kao Corporation, NS Soap) 3 parts by weight and potassium stearate (made by NOF Corporation, NONSOUL SK-1) 0.5 part by weight were added and the result kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 7.

Example 4-2

Except for changing the amount of the compound 1 (antiaging agent) to 2.00 parts, the same procedure was followed as in Example 4-1 to obtain an acrylic rubber composition and similarly evaluate it. The results are shown in Table 7.

Example 4-3

Chlorine atom-containing acrylic rubber (made by Zeon Corporation, Nipol AR71) 100 parts by weight, carbon black (made by Tokai Carbon, Seast SO) 50 parts by weight, stearic acid 2 parts by weight, and the compound 1 (antiaging agent), which was obtained by the above-mentioned Manufacturing Example 1, 1.00 parts by weight were kneaded using a 0.8 liter Bambury mixer at 50° C. for 5 minutes, then a cross-linking agent constituted by 2,4,6-trimercapto-s-triazine (made by Sankyo Chemical, ZISNET F) 0.5 part by weight, cross-linking accelerators constituted by zinc di-n-butyldithiocarbamate (made by Ouchi Shinko Chemical Industrial, Nocceler BZ) 1.5 parts by weight and N,N'-diethyl thiourea (made by Ouchi Shinko Chemical Industrial, Nocceler EUR) 0.3 part by weight, and a scorch retarder constituted by n-cyclohexylthiophthalimide (made by Ouchi Shinko Chemical Industrial, Retarder CTP) 0.2 part by weight were added and the result kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 7.

Example 4-4

Except for changing the amount of the compound 1 (antiaging agent) to 2.00 parts, the same procedure was followed as in Example 4-3 to obtain an acrylic rubber composition and similarly evaluate it. The results are shown in Table 7.

Comparative Example 4-1

Except for using, instead of the compound 1 (antiaging agent), 4,4'-bis(α,α-dimethylbenzyl)diphenylamine (antiaging agent, made by Chemtura, Nauguard 445) and making the amount 2.00 parts, the same procedure was followed as in Example 4-1 to obtain an acrylic rubber composition and similarly evaluate it. The results are shown in Table 7.

Comparative Example 4-2

Except for using, instead of the compound 1 (antiaging agent), 4,4'-bis(α,α-dimethylbenzyl)diphenylamine (antiaging agent, made by Chemtura, Nauguard 445) and making the amount 2.00 parts, the same procedure was followed as in Example 4-3 to obtain an acrylic rubber composition and similarly evaluate it. The results are shown in Table 7.

(Test of Original Properties)

The same procedures were performed as in Examples 1-1 to 1-8 and Comparative Examples 1-1 to 1-4 to obtain test pieces and measure the tensile strength (strength), elongation at break (elongation), modulus at 100%, and hardness.

(Heat Resistance Test)

The heat resistance test was performed by heating a test piece, which was prepared in the same way as the test of original properties, in a 175° C. environment for 1000 hours to cause heat aging and by using that piece. Specifically, first, the elongations before and after heating were measured in accordance with JIS K6251, then the following formula was used to calculate the rate of change to thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

TABLE 7

| Formulation | | Ex. 4-1 | Ex. 4-2 | Ex. 4-3 | Ex. 4-4 | Comp. Ex. 4-1 | Comp. Ex. 4-2 |
|---|---|---|---|---|---|---|---|
| Chlorine atom-containing acrylic rubber (Nipol AR71) | Parts by weight | 100 | 100 | 100 | 100 | 100 | 100 |
| Carbon black | Parts by weight | 50 | 50 | 50 | 50 | 50 | 50 |
| Stearic acid | Parts by weight | 2 | 2 | 2 | 2 | 2 | 2 |
| Antiaging agent | Type | Compound 1 | | | | 4,4'-bis(α,α-dimethylbenzyl)-diphenylamine | |
| Amount of addition to rubber 100 parts by weight | Parts by weight | 1.00 | 2.00 | 1.00 | 2.00 | 2.00 | 2.00 |
| Sulfur | Parts by weight | 0.3 | 0.3 | — | — | 0.3 | — |
| Sodium stearate | Parts by weight | 3 | 3 | — | — | 3 | — |
| Potassium stearate | Parts by weight | 0.5 | 0.5 | — | — | 0.5 | — |
| 2,4,6-trimercapto-s-triazine | Parts by weight | — | — | 0.5 | 0.5 | — | 0.5 |
| Zinc di-n-butyldithiocarbmate | Parts by weight | — | — | 1.5 | 1.5 | — | 1.5 |
| N,N'-diethylthioureic acid | Parts by weight | — | — | 0.3 | 0.3 | — | 0.3 |
| N-cyclohexylthiophthalimide | Parts by weight | — | — | 0.2 | 0.2 | — | 0.2 |
| Original properties | Tensile strength [MPa] | 12.9 | 12.9 | 11.7 | 11.6 | 12.4 | 10.6 |
| | Elongation [%] | 324 | 335 | 260 | 275 | 336 | 259 |
| | 100% modulus [MPa] | 4.1 | 3.9 | 4.7 | 4.4 | 3.8 | 4.1 |
| | Hardness [Duro A] | 65 | 66 | 69 | 67 | 64 | 66 |
| Heat resistance test | Rate of change of elongation [%] After 190° C. 500 hours | −71 | −46 | −27 | −37 | −89 | −83 |

Evaluation of Examples 4-1 to 4-4 and Comparative Examples 4-1, 4-2

As shown in Table 7, in Examples 4-1 to 4-4 which used antiaging agents constituted by predetermined compound 1 of the present invention, even after going through severe conditions of an environment of 190° C. for 500 hours, compared with Comparative Examples 4-1 and 4-2, the rates of change of elongation were close to 0 and the changes in elongation were small. Accordingly, it was confirmed that the cross-linked rubber products which were obtained by using the acrylic rubber compositions of the present invention were improved in heat resistance in the heat resistance test regardless of the type of the cross-linking agents and cross-linking accelerators.

Methods of Evaluation of Examples 5-1 to 5-3 and Comparative Examples 5-1, 5-2

The various tests of the physical properties in Examples 5-1 to 5-3 and Comparative Examples 5-1, 5-2 were performed by the following methods.

Example 5-1

The carboxyl group- and chlorine atom-containing acrylic rubber C, which was obtained by the Manufacturing Example 3 of the above-mentioned acrylic rubber, 100 parts by weight, carbon black (made by Tokai Carbon, Seast SO) 50 parts by weight, stearic acid 2 parts by weight, and the compound 1 (antiaging agent), which was obtained by the Manufacturing Example 1 of the above-mentioned compound, 1.00 part by weight were kneaded using a 0.8 liter Bambury mixer at 50° C. for 5 minutes, then a cross-linking agent constituted by sulfur (made by Tsurumi Chemical Industry, Sulfax PMC) 0.3 part by weight, and cross-linking accelerators constituted by sodium stearate (made by Kao Corporation, NS Soap) 3 parts by weight and potassium stearate (made by NOF Corporation, NONSOUL SK-1) 0.5 part by weight were added, then the mixture was kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 8.

Example 5-2

Except for changing the amount of the compound 1 (antiaging agent) to 2.00 parts, the same procedure was followed as in Example 5-1 to obtain an acrylic rubber composition and similarly evaluate it. The results are shown in Table 8.

Example 5-3

Except for further adding a cross-linking agent constituted by hexamethylenediamine carbamate (made by Dupont Dow Elastomer Japan, Diak No. 1) 0.2 part by weight and a cross-linking accelerator constituted by 1,3-di-o-tolylguanidine (made by Ouchi Shinko Chemical Industrial, Nocceler DT) 0.5 part by weight, the same procedure was followed as in Example 5-1 to obtain an acrylic rubber composition and similarly evaluate it. The results are shown in Table 8.

Comparative Example 5-1

Except for using, instead of the compound 1 (antiaging agent), 4,4'-bis(α,α-dimethylbenzyl)diphenylamine (antiaging agent, made by Chemtura, Nauguard 445) and making the amount 2.00 parts, the same procedure was followed as in Example 5-1 to obtain an acrylic rubber composition and similarly evaluate it. The results are shown in Table 8.

Comparative Example 5-2

Except for using, instead of the compound 1 (antiaging agent), 4,4'-bis(α,α-dimethylbenzyl)diphenylamine (antiaging agent, made by Chemtura, Nauguard 445) and making the amount 2.00 parts, the same procedure was followed as in Example 5-3 to obtain an acrylic rubber composition and similarly evaluate it. The results are shown in Table 8.

were small. Further, in the same way as Examples 5-1 and 5-2, in Example 5-3 as well, which used an antiaging agent constituted by a predetermined compound 1 of the present invention, compared with Comparative Example 5-2, which used a similar cross-linking agent in the same amount, but had an antiaging agent of a conventional compound, the rate of change of elongation was close to 0 and the change in elongation was small. Accordingly, it was confirmed that the cross-linked rubber products which were obtained by using the acrylic rubber compositions of the present invention were improved in heat resistance in the heat resistance test regardless of the type of the cross-linking agents and cross-linking accelerators.

Methods of Evaluation of Examples 6-1 to 6-11 and Comparative Examples 6-1 to 6-4

The various tests of the physical properties in Examples 6-1 to 6-11 and Comparative Examples 6-1 to 6-4 were performed by the following methods.

(Test of Original Properties)

The same procedures were performed as in Examples 1-1 to 1-8 and Comparative Examples 1-1 to 1-4 to obtain test pieces and measure the tensile strength (strength), elongation at break (elongation), modulus at 100%, and hardness.

(Heat Resistance Test)

The heat resistance test was performed by heating a test piece, which was prepared in the same way as the test of original properties, in a 175° C. or 190° C. environment for 500 hours to cause heat aging and by using that piece. Specifically, first, the elongations before and after heating were measured in accordance with JIS K6251, then the following formula was used to calculate the rate of change to thereby measure the rate of change of elongation. The closer the rate

TABLE 8

| Formulation | | Ex. 5-1 | Ex. 5-2 | Ex. 5-3 | Comp. Ex. 5-1 | Comp. Ex. 5-2 |
|---|---|---|---|---|---|---|
| Carboxyl group- and chlorine atom-containing acrylic rubber C | Parts by weight | 100 | 100 | 100 | 100 | 100 |
| Carbon black | Parts by weight | 50 | 50 | 50 | 50 | 50 |
| Stearic acid | Parts by weight | 2 | 2 | 2 | 2 | 2 |
| Antiaging agent Type | | Compound 1 | Compound 1 | Compound 1 | 4,4'-bis(α,α-dimethylbenzyl)diphenylamine | 4,4'-bis(α,α-dimethylbenzyl)diphenylamine |
| Amount of addition to rubber 100 parts by weight | Parts by weight | 1.00 | 2.00 | 1.00 | 2.00 | 2.00 |
| Sulfur | Parts by weight | 0.3 | 0.3 | 0.3 | 0.3 | 0.3 |
| Sodium stearate | Parts by weight | 3 | 3 | 3 | 3 | 3 |
| Potassium stearate | Parts by weight | 0.5 | 0.5 | 0.5 | 0.5 | 0.5 |
| Hexamethylenediamine carbamate | Parts by weight | — | — | 0.2 | — | 0.2 |
| 1,3-di-o-tolylguanidine | Parts by weight | — | — | 0.5 | — | 0.5 |
| Original properties | Tensile strength [MPa] | 13.6 | 13.1 | 14.4 | 12.8 | 14.5 |
| | Elongation [%] | 290 | 280 | 210 | 300 | 210 |
| | 100% modulus [MPa] | 4.1 | 4.2 | 6.4 | 3.8 | 6.5 |
| | Hardness [Duro A] | 73 | 74 | 63 | 72 | 63 |
| Heat resistance test | Rate of change of elongation [%] After 175° C. 1000 hours | −52 | −46 | −33 | −63 | −52 |

Evaluation of Examples 5-1 to 5-3 and Comparative Examples 5-1, 5-2

As shown in Table 8, in Examples 5-1 and 5-2 which used antiaging agents constituted by predetermined compound 1 of the present invention, even after going through severe conditions of an environment of 175° C. for 1000 hours, compared with Comparative Example 5-1, which used a similar cross-linking agent in the same amount, but had an antiaging agent of a conventional compound, the rates of change of elongation were close to 0 and the changes in elongation of change of elongation to zero, the higher the heat resistance is judged and the more preferable the result.

Rate of change of elongation (%)=100×[(elongation after heating (%))−(elongation before heating (%))]/(elongation before heating (%))

Example 6-1

The carboxyl group-containing ethylene-acrylate rubber a (made by Dupont, Vamac G) 100 parts by weight, carbon black (made by Tokai Carbon, Seast SO) 50 parts by weight, stearic acid 2 parts by weight, and the compound 1 (antiaging agent), which was obtained by the above-mentioned Manufacturing Example 1, 1.00 part by weight were kneaded using a 0.8 liter Bambury mixer at 50° C. for 5 minutes, then a cross-linking agent constituted by 2,2-bis[4-(4-amino phenoxy)phenyl]propane (made by Wakayama Seika Kogyo, BAPP) 2.5 parts by weight and a cross-linking accelerator constituted by dialkyl($C_8$ to $C_{18}$)amine (made by Lion Akzo, Armeen 2C) 3 parts by weight were added and the result kneaded by open roll at 50° C. to prepare an acrylic rubber composition. Further, the obtained acrylic rubber composition was used in accordance with the above methods to perform a test on the original properties and a heat resistance test (175° C., 500 hours) constituted by measurement of the rate of change of elongation. The results are shown in Table 9.

Example 6-2

Except for changing the amount of the compound 1 (antiaging agent) to 2.00 parts, the same procedure was followed as in Example 6-1 to obtain an acrylic rubber composition and similarly evaluate it. The results are shown in Table 9.

Example 6-3

The carboxyl group-containing ethylene-acrylate rubber b (made by DENKA, Denka ER-A403) 100 parts by weight, tance test (190° C., 500 hours) constituted by measurement of the rate of change of elongation. The results are shown in Table 9.

Example 6-4

Except for changing the amount of the compound 1 (antiaging agent) to 2.00 parts, the same procedure was followed as in Example 6-3 to obtain an acrylic rubber composition and similarly evaluate it. The results are shown in Table 9.

Comparative Example 6-1

Except for using, instead of the compound 1 (antiaging agent), 4,4'-bis($\alpha,\alpha$-dimethylbenzyl)diphenylamine (antiaging agent, made by Chemtura, Nauguard 445) and making the amount 2.00 parts, the same procedure was followed as in Example 6-1 to obtain an acrylic rubber composition and similarly evaluate it. The results are shown in Table 9.

Comparative Example 6-2

Except for using, instead of the compound 1 (antiaging agent), 4,4'-bis($\alpha,\alpha$-dimethylbenzyl)diphenylamine (antiaging agent, made by Chemtura, Nauguard 445) and making the amount 2.00 parts, the same procedure was followed as in Example 6-3 to obtain an acrylic rubber composition and similarly evaluate it. The results are shown in Table 9.

TABLE 9

| | Formulation | | Ex. 6-1 | Ex. 6-2 | Ex. 6-3 | Ex. 6-4 | Comp. Ex. 6-1 | Comp. Ex. 6-2 |
|---|---|---|---|---|---|---|---|---|
| Acrylic rubber | Carboxyl group-containing ethylene-acrylate rubber a (Vamac G) | Parts by weight | 100 | 100 | — | — | 100 | — |
| | Carboxyl group-containing ethylene-acrylate rubber b (Denka ER-A403) | Parts by weight | — | — | 100 | 100 | — | 100 |
| | Carbon black | Parts by weight | 50 | 50 | 55 | 55 | 50 | 55 |
| | Stearic acid | Parts by weight | 2 | 2 | 2 | 2 | 2 | 2 |
| Antiaging agent | Type | | Compound 1 | | | | 4,4'-bis($\alpha,\alpha$-dimethylbenzyl)diphenylamine | |
| | Amount of addition to rubber 100 parts by weight | Parts by weight | 1.00 | 2.00 | 1.00 | 2.00 | 2.00 | 2.00 |
| 2,2-bis[4-(4-aminophenoxy)phenyl]propane | | Parts by weight | 2.5 | 2.5 | 1 | 1 | 2.5 | 1 |
| Dialkyl($C_8$ to $C_{18}$)amine | | Parts by weight | 3 | 3 | 2 | 2 | 3 | 2 |
| Original properties | Tensile strength [MPa] | | 13.9 | 14.8 | 10.6 | 10.4 | 14.6 | 10.2 |
| | Elongation [%] | | 370 | 420 | 270 | 260 | 430 | 270 |
| | 100% modulus [MPa] | | 3.8 | 3.4 | 3.9 | 3.7 | 3.4 | 3.9 |
| | Hardness [Duro A] | | 75 | 75 | 65 | 63 | 73 | 64 |
| Heat resistance test | Rate of change of elongation [%] After 175° C. 500 hours | | −59 | −55 | — | — | −65 | — |
| | Rate of change of elongation [%] After 190° C. 500 hours | | — | — | −59 | −54 | — | −81 | carbon black (made by Tokai Carbon, Seast SO) 55 parts by weight, stearic acid 2 parts by weight, and the compound 1 (antiaging agent), which was obtained by the above-mentioned Manufacturing Example 1, 1.00 part by weight were kneaded using a 0.8 liter Bambury mixer at 50° C. for 5 minutes, then a cross-linking agent constituted by 2,2-bis[4-(4-amino phenoxy)phenyl]propane (made by Wakayama Seika Kogyo, BAPP) 1 part by weight and a cross-linking accelerator constituted by dialkyl($C_8$ to $C_{18}$)amine (made by Lion Akzo, Armeen 2C) 2 parts by weight were added and the result kneaded by open roll at 50° C. to prepare an acrylic rubber composition. Further, the obtained acrylic rubber composition was used in accordance with the above methods to perform a test on the original properties and a heat resis- Evaluation of Examples 6-1 to 6-4 and Comparative Examples 6-1, 6-2

As shown in Table 9, in Examples 6-1 to 6-4 which used antiaging agents constituted by predetermined compound 1 of the present invention, even after going through severe conditions of an environment of 175° C. or 190° C. for 500 hours, compared with Comparative Example 6-1 or 6-2, the rates of change of elongation were close to 0 and the changes in elongation were small. Accordingly, it was confirmed that the cross-linked rubber products which were obtained by using the acrylic rubber compositions of the present invention were improved in heat resistance in the heat resistance test.

Example 6-5

Carboxyl group-containing ethylene-acrylate rubber a (made by Dupont, Vamac G) 100 parts by weight, carbon black (made by Tokai Carbon, Seast SO) 45 parts by weight, stearic acid 2 parts by weight, and the compound 1 (antiaging agent), which was obtained by Manufacturing Example 1 of the above-mentioned compound, 1.00 parts by weight were kneaded using a 0.8 liter Bambury mixer at 50° C. for 5 minutes, then a cross-linking agent constituted by hexamethylenediamine carbamate (made by Dupont Dow Elastomer Japan, Diak No. 1) 1.5 parts by weight and a cross-linking accelerator constituted by 1,3-di-o-tolylguanidine (made by Ouchi Shinko Chemical Industrial, Nocceler DT) 4 parts by weight were added and the result kneaded by open roll at 50° C. to prepare an acrylic rubber composition. Further, the obtained acrylic rubber composition was used in accordance with the above methods to perform a test on the original properties and a heat resistance test (175° C., 500 hours) constituted by measurement of the rate of change of elongation. The results are shown in Table 10.

Example 6-6

Except for making the amount of the compound 1 (antiaging agent) 2.00 parts, the same procedure was followed as in Example 6-5 to obtain an acrylic rubber composition and similarly evaluate it. The results are shown in Table 10.

Further, the obtained acrylic rubber composition was used in accordance with the above methods to perform a test on the original properties and a heat resistance test (190° C., 500 hours) constituted by measurement of the rate of change of elongation. The results are shown in Table 10.

Example 6-8

Except for changing the amount of the compound 1 (antiaging agent) to 2.00 parts, the same procedure was followed as in Example 6-7 to obtain an acrylic rubber composition and similarly evaluate it. The results are shown in Table 10.

Comparative Example 6-3

Except for using, instead of the compound 1 (antiaging agent), 4,4'-bis($\alpha,\alpha$-dimethylbenzyl)diphenylamine (antiaging agent, made by Chemtura, Nauguard 445) and making the amount 2.00 parts, the same procedure was followed as in Example 6-5 to obtain an acrylic rubber composition and similarly evaluate it. The results are shown in Table 10.

Comparative Example 6-4

Except for using, instead of the compound 1 (antiaging agent), 4,4'-bis($\alpha,\alpha$-dimethylbenzyl)diphenylamine (antiaging agent, made by Chemtura, Nauguard 445) and making the amount 2.00 parts, the same procedure was followed as in Example 6-7 to obtain an acrylic rubber composition and similarly evaluate it. The results are shown in Table 10.

TABLE 10

| Formulation | | | Ex. 6-5 | Ex. 6-6 | Ex. 6-7 | Ex. 6-8 | Comp. Ex. 6-3 | Comp. Ex. 6-4 |
|---|---|---|---|---|---|---|---|---|
| Acrylic rubber | Carboxyl group-containing ethylene-acrylate rubber a (Vamac G) | Parts by weight | 100 | 100 | — | — | 100 | — |
| | Carboxyl group-containing ethylene-acrylate rubber b (Denka ER-A403) | Parts by weight | — | — | 100 | 100 | — | 100 |
| | Carbon black | Parts by weight | 45 | 45 | 50 | 50 | 45 | 50 |
| | Stearic acid | Parts by weight | 2 | 2 | 2 | 2 | 2 | 2 |
| Antiaging agent | Type | | Compound 1 | | | | 4,4'-bis($\alpha,\alpha$-dimethylbenzyl)diphenylamine | |
| | Amount of addition to rubber 100 parts by weight | Parts by weight | 1.00 | 2.00 | 1.00 | 2.00 | 2.00 | 2.00 |
| Hexamethylenediamine carbamate | | Parts by weight | 1.5 | 1.5 | 0.6 | 0.6 | 1.5 | 0.6 |
| 1,3-di-o-tolylguanidine | | Parts by weight | 4.0 | 4.0 | 1.5 | 1.5 | 4.0 | 1.5 |
| Original properties | | Tensile strength [MPa] | 15.7 | 15.0 | 11.2 | 11.0 | 15.8 | 10.8 |
| | | Elongation [%] | 330 | 330 | 220 | 230 | 360 | 220 |
| | | 100% modulus [MPa] | 4.1 | 3.8 | 4.6 | 4.2 | 3.4 | 4.6 |
| | | Hardness [Duro A] | 69 | 69 | 64 | 64 | 66 | 64 |
| Heat resistance test | | Rate of change of elongation [%] After 175° C. 500 hours | −52 | −45 | — | — | −61 | — |
| | | Rate of change of elongation [%] After 190° C. 500 hours | — | — | −55 | −48 | — | −77 |

(Example 6-7)

Carboxyl group-containing ethylene-acrylate rubber b (made by DENKA, Denka ER-A403) 100 parts by weight, carbon black (made by Tokai Carbon, Seast SO) 50 parts by weight, stearic acid 2 parts by weight, and the compound 1 (antiaging agent), which was obtained by the Manufacturing Example 1 of the above-mentioned compound, 1.00 part by weight were kneaded using a 0.8 liter Bambury mixer at 50° C. for 5 minutes, then a cross-linking agent constituted by hexamethylenediamine carbamate (made by Dupont Dow Elastomer Japan, Diak No. 1) 0.6 part by weight and a cross-linking accelerator constituted by 1,3-di-o-tolylguanidine (made by Ouchi Shinko Chemical Industrial, Nocceler DT) 1.5 parts by weight were added and the result kneaded by open roll at 50° C. to prepare an acrylic rubber composition.

Evaluation of Examples 6-5 to 6-8 and Comparative Examples 6-3, 6-4

As shown in Table 10, in Examples 6-5 to 6-8 which used antiaging agents constituted by predetermined compound 1 of the present invention, even after going through severe conditions of an environment of 175° C. or 190° C. for 500 hours, compared with Comparative Example 6-3 or 6-4, the rates of change of elongation were close to 0 and the changes in elongation were small. Accordingly, it was confirmed that the cross-linked rubber products which were obtained by using the acrylic rubber compositions of the present invention were improved in heat resistance in the heat resistance test regardless of the types of the cross-linking agents and cross-linking accelerators.

Example 6-9

The carboxyl group-containing acrylic rubber A, which was obtained by the above-mentioned Manufacturing Example 1 of acrylic rubber, 75 parts by weight, and carboxyl group-containing ethylene-acrylate rubber b (made by DENKA, Denka ER-A403) 25 parts by weight (carboxyl group-containing acrylic rubber A and carboxyl group-containing ethylene-acrylate rubber b combined to give 100 parts by weight as acrylic rubber), carbon black (made by Tokai Carbon, Seast SO) 60 parts by weight, stearic acid 2 parts by weight, and the compound 1 (antiaging agent), which was obtained by the above-mentioned Manufacturing Example 1, 1.00 part by weight were kneaded using a 0.8 liter Bambury mixer at 50° C. for 5 minutes, then a cross-linking agent constituted by 2,2-bis[4-(4-amino phenoxy)phenyl]propane (made by Wakayama Seika Kogyo, BAPP) 1 part by weight and a cross-linking accelerator constituted by dialkyl($C_8$ to $C_{18}$)amine (made by Lion Akzo, Armeen 2C) 2 parts by weight were added and the result kneaded by open roll at 50° C. to prepare an acrylic rubber composition. Further, the obtained acrylic rubber composition was used in accordance with the above methods to perform a test on the original properties and a heat resistance test (190° C., 500 hours) constituted by measurement of the rate of change of elongation. The results are shown in Table 11.

Examples 6-10, 6-11

Except for changing the amount of the acrylic rubber to the carboxyl group-containing acrylic rubber A 50 parts by weight and carboxyl group-containing ethylene-acrylate rubber b (made by DENKA, Denka ER-A403) 50 parts by weight (Example 6-10) and to the carboxyl group-containing acrylic rubber A 25 parts by weight and carboxyl group-containing ethylene-acrylate rubber b (made by DENKA, Denka ER-A403) 75 parts by weight (Example 6-11), the same procedures were followed as in Example 6-9 to obtain acrylic rubber compositions and similarly evaluate them. The results are shown in Table 11.

changes of elongation were small. Accordingly, it was confirmed that the cross-linked rubber products obtained by using the acrylic rubber compositions of the present invention were superior in heat resistance in the heat resistance test regardless of using mixtures of ones having ethylene and ones not having it as the monomers forming the acrylic rubber.

Methods of Evaluation of Examples 7-1 to 7-11 and Comparative Examples 7-1 to 7-8

The various tests of the physical properties in Examples 7-1 to 7-11 and Comparative Examples 7-1 to 7-8 were performed by the following methods.

(Test of Original Properties)

The same procedures were performed as in Examples 1-1 to 1-8 and Comparative Examples 1-1 to 1-4 to obtain test pieces and measure the tensile strength (strength), elongation at break (elongation), modulus at 100%, and hardness.

(Heat Resistance Test)

The heat resistance test was performed by heating a test piece, which was prepared in the same way as the test of original properties, in a 190° C. environment for 500 hours to cause heat aging and by using that piece. Specifically, first, the elongations before and after heating were measured in accordance with JIS K6251, then the following formula was used to calculate the rate of change to thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

Example 7-1

Carboxyl group-containing acrylic rubber A, which was obtained by the above-mentioned Manufacturing Example 1 of acrylic rubber, 100 parts by weight, carbon black (made by Tokai Carbon, Seast SO) 66 parts by weight, stearic acid 2

TABLE 11

| | Formulation | | Ex. 6-9 | Ex. 6-10 | Ex. 6-11 |
|---|---|---|---|---|---|
| Acrylic rubber | Carboxyl group-containing acrylic rubber A | Parts by weight | 75 | 50 | 25 |
| | Carboxyl group-containing ethylene-acrylate rubber b (Denka ER-A403) | Parts by weight | 25 | 50 | 75 |
| | Carbon black | Parts by weight | 60 | 60 | 60 |
| | Stearic acid | Parts by weight | 2 | 2 | 2 |
| Antiaging agent | Type | | Compound 1 | | |
| | Amount of addition to rubber 100 parts by weight | Parts by weight | 1.00 | 1.00 | 1.00 |
| | 2,2-bis[4-(4-aminophenoxy)phenyl] propane | Parts by weight | 1 | 1 | 1 |
| | Dialkyl($C_8$ to $C_{18}$)amine | Parts by weight | 2 | 2 | 2 |
| | Original properties | Tensile strength [MPa] | 9.4 | 9.3 | 10.1 |
| | | Elongation [%] | 270 | 260 | 250 |
| | | 100% modulus [MPa] | 3.5 | 3.7 | 4.3 |
| | | Hardness [Duro A] | 64 | 64 | 66 |
| | Heat resistance test | Rate of change of elongation [%] After 190° C. 500 hours | −63 | −65 | −64 |

As shown in Table 11, in Examples 6-9 to 6-11 which used antiaging agents constituted by predetermined compound 1 of the present invention, even after going through severe conditions of an environment of 190° C. for 500 hours, the rates of change of elongation were suppressed and the parts by weight, and antiaging agents constituted by the compound 1, which was obtained by the Manufacturing Example 1 of the above-mentioned compound, 1.00 part by weight and 4,4'-bis(α,α-dimethylbenzyl)diphenylamine (made by Chemtura, Nauguard 445) 2.00 parts by weight were kneaded using a 0.8 liter Bambury mixer at 50° C. for 5 minutes, then a cross-linking agent constituted by 2,2-bis[4-(4-amino phenoxy)phenyl]propane (made by Wakayama Seika Kogyo, BAPP) 1 part by weight and a cross-linking accelerator constituted by dialkyl($C_8$ to $C_{18}$)amine (made by Lion Akzo, Armeen 2C) 2 parts by weight were added and the result kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 12.

Example 7-2

Except for using, instead of 4,4'-bis($\alpha,\alpha$-dimethylbenzyl)diphenylamine 2.00 parts, 2,2'-methylene bis(4-methyl-6-t-butylphenol) (made by Ouchi Shinko Chemical Industrial, Nocrac NS-6) 1.00 part and, further, making the amount of the compound 1 not 1.00 part, but 3.00 parts, the same procedure was followed as in Example 7-1 to obtain an acrylic rubber composition and similarly evaluate it. The results are shown in Table 12.

Example 7-3

Except for using, instead of 4,4'-bis($\alpha,\alpha$-dimethylbenzyl)diphenylamine 2.00 parts, 2-mercaptobenzimidazole (made by Ouchi Shinko Chemical Industrial, Nocrac MB) 1.00 part and, further, making the amount of the compound 1 not 1.00 part, but 3.00 parts, the same procedure was followed as in Example 7-1 to obtain an acrylic rubber composition and similarly evaluate it. The results are shown in Table 12.

Comparative Example 7-1

Except for not adding the compound 1, the same procedure was followed as in Example 7-1 to obtain an acrylic rubber composition and similarly evaluate it. The results are shown in Table 12.

and other antiaging agent, even after going through severe conditions of an environment of 190° C. for 500 hours, compared with Comparative Example 7-1, the rates of change of elongation were close to 0 and the changes in elongation were small. Accordingly, it was confirmed that the cross-linked rubber products which are obtained by using the acrylic rubber compositions of the present invention are improved in heat resistance in the heat resistance test.

Example 7-4

The carboxyl group-containing acrylic rubber B, which obtained by the above-mentioned Manufacturing Example 2 of acrylic rubber, 100 parts by weight, carbon black (made by Tokai Carbon, Seast SO) 60 parts by weight, stearic acid 2 parts by weight, and antiaging agents constituted by the compound 1, which was obtained by the above-mentioned Manufacturing Example 1 of the compound, 1.00 part by weight and 4,4'-bis($\alpha,\alpha$-dimethylbenzyl)diphenylamine (made by Chemtura, Nauguard 445) 1.00 part by weight were kneaded using a 0.8 liter Banbury mixer at 50° C. for 5 minutes, then a cross-linking agent constituted by hexamethylenediamine carbamate (made by Dupont Dow Elastomer Japan, Diak No. 1) 0.6 part by weight and a cross-linking accelerator constituted by 1,3-di-o-tolylguanidine (made by Ouchi Shinko Chemical Industrial, Nocceler DT) 2 parts by weight were added and the result kneaded by open roll at 50° C. to prepare an acrylic rubber composition. Further, the obtained acrylic rubber composition was used in accordance with the above methods to perform a test on the original properties and a heat resistance test constituted by measurement of the rate of change of elongation. The results are shown in Table 13.

Examples 7-5 to 7-11

Except for changing 4,4'-bis($\alpha,\alpha$-dimethylbenzyl)diphenylamine 1.00 part to N,N'-di-2-naphthyl-p-phenylenediamine 1.00 part (made by Ouchi Shinko Chemical Industrial, Nocrac White) (Example 7-5), 2,2'-methylene bis(4-methyl-

TABLE 12

| Formulation | | Ex. 7-1 | Ex. 7-2 | Ex. 7-3 | Comp. Ex. 7-1 |
|---|---|---|---|---|---|
| Carboxyl group-containing acrylic rubber A | Parts by weight | 100 | 100 | 100 | 100 |
| Carbon black | Parts by weight | 66 | 66 | 66 | 66 |
| Stearic acid | Parts by weight | 2 | 2 | 2 | 2 |
| Antiaging agent | Type | Compound 1 | | | — |
| | Amount of addition to rubber 100 parts by weight | Parts by weight | 1.00 | 3.00 | 3.00 | — |
| | Type | | 4,4'-bis($\alpha,\alpha$-dimethylbenzyl)diphenylamine | 2,2'-methylenebis(4-methyl-6-t-butylphenol) | 2-mercaptobenzimidazole | 4,4'-bis($\alpha,\alpha$-dimethylbenzyl)diphenylamine |
| | Amount of addition to rubber 100 parts by weight | Parts by weight | 2.00 | 1.00 | 1.00 | 2.00 |
| 2,2-bis[4-(4-aminophenoxy)phenyl]propane | Parts by weight | 1 | 1 | 1 | 1 |
| Dialkyl($C_8$ to $C_{18}$)amine | Parts by weight | 2 | 2 | 2 | 2 |
| Original properties | Tensile strength [MPa] | 10.2 | 9.1 | 9.1 | 9.8 |
| | Elongation [%] | 270 | 210 | 310 | 270 |
| | 100% modulus [MPa] | 3.5 | 3.5 | 2.8 | 3.6 |
| | Hardness [Duro A] | 67 | 63 | 63 | 66 |
| Heat resistance test | Rate of change of elongation [%] After 190° C. .500 hours | −59 | −38 | −61 | −78 |

Evaluation of Examples 7-1 to 7-3 and Comparative Example 7-1

As shown in Table 12, in Examples 7-1 to 7-3 which jointly use the predetermined compound 1 of the present invention 6-t-butylphenol) 1.00 part (made by Ouchi Shinko Chemical Industrial, Nocrac NS-6) (Example 7-6), 2,6-di-t-butyl-4-methylphenol 1.00 part (made by Ouchi Shinko Chemical Industrial, Nocrac 200) (Example 7-7), 2,6-di-t-butyl-4-methylphenol 2.00 part (made by Ouchi Shinko Chemical Industrial, Nocrac 200) (Example 7-8), 2-mercaptobenzimidazole 1.00 part (made by Ouchi Shinko Chemical Industrial, Nocrac MB) (Example 7-9), tris(nonylphenyl)phosphite 1.00 part (made by Ouchi Shinko Chemical Industrial, Nocrac TNP) (Example 7-10), and tris(nonylphenyl)phosphite 1.00 part (made by Ouchi Shinko Chemical Industrial, Nocrac TNP) and 2-mercaptobenzimidazole 0.50 part (made by Ouchi Shinko Chemical Industrial, Nocrac MB) (Example 7-11), the same procedures was followed as in Example 7-4 to obtain acrylic rubber compositions and similarly evaluate them. The results are shown in Table 13.

TABLE 13

| Formulation | | Ex. 7-4 | Ex. 7-5 | Ex. 7-6 | Ex. 7-7 | Ex. 7-8 |
|---|---|---|---|---|---|---|
| Carboxyl group-containing acrylic rubber B | Parts by weight | 100 | 100 | 100 | 100 | 100 |
| Carbon black | Parts by weight | 60 | 60 | 60 | 60 | 60 |
| Stearic acid | Parts by weight | 2 | 2 | 2 | 2 | 2 |
| Antiaging agent | Type | Compound 1 | | | | |
| | Amount of addition to rubber 100 parts by weight | Parts by weight | 1.00 | | | | |
| | Type | 4,4'-bis(α,α-dimethylbenzyl)-diphenylamine | N,N'-di-2-naphthyl-p-phenylenediamine | 2,2'-methylenebis(4-methyl-6-t-butylphenol) | 2,6-di-t-butyl-4-methylphenol | |
| | Amount of addition to rubber 100 parts by weight | Parts by weight | 1.00 | 1.00 | 1.00 | 1.00 | 2.00 |
| | Type | — | — | — | — | — |
| | Amount of addition to rubber 100 parts by weight | Parts by weight | — | — | — | — | — |
| Hexamethylenediamine carbamate | Parts by weight | 0.6 | 0.6 | 0.6 | 0.6 | 0.6 |
| 1,3-di-o-tolylguanidine | Parts by weight | 2 | 2 | 2 | 2 | 2 |
| Original properties | Tensile strength [MPa] | 9.0 | 8.7 | 9.7 | 9.6 | 10.0 |
| | Elongation [%] | 190 | 180 | 200 | 190 | 190 |
| | 100% modulus [MPa] | 4.5 | 4.6 | 5.5 | 5.4 | 5.5 |
| | Hardness [Duro A] | 68 | 70 | 72 | 72 | 68 |
| Heat resistance test | Rate of change of elongation [%] After 190° C. 500 hours | −42 | −44 | −55 | −53 | −47 |

| Formulation | | Ex. 7-9 | Ex. 7-10 | Ex. 7-11 |
|---|---|---|---|---|
| Carboxyl group-containing acrylic rubber B | Parts by weight | 100 | 100 | 100 |
| Carbon black | Parts by weight | 60 | 60 | 60 |
| Stearic acid | Parts by weight | 2 | 2 | 2 |
| Antiaging agent | Type | Compound 1 | | |
| | Amount of addition to rubber 100 parts by weight | Parts by weight | 1.00 | | |
| | Type | 2-mercaptobenzimidazole | Tris(nonylphenyl)phosphite | |
| | Amount of addition to rubber 100 parts by weight | Parts by weight | 1.00 | 1.00 | 1.00 |
| | Type | — | — | 2-mercaptobenzimidazole |
| | Amount of addition to rubber 100 parts by weight | Parts by weight | — | — | 0.50 |
| Hexamethylenediamine carbamate | Parts by weight | 0.6 | 0.6 | 0.6 |
| 1,3-di-o-tolylguanidine | Parts by weight | 2 | 2 | 2 |
| Original properties | Tensile strength [MPa] | 9.9 | 9.0 | 8.9 |
| | Elongation [%] | 210 | 240 | 230 |
| | 100% modulus [MPa] | 5.8 | 3.6 | 4.1 |
| | Hardness [Duro A] | 72 | 69 | 71 |
| Heat resistance test | Rate of change of elongation [%] After 190° C. 500 hours | −57 | −54 | −57 |

Comparative Example 7-2

Except for not adding the compound 1 and making the amount of 4,4'-bis(α,α-dimethylbenzyl)diphenylamine not 1.00 part but 2.00 parts, the same procedure was followed as in Example 7-4 to obtain an acrylic rubber composition and similarly evaluate it. The results are shown in Table 14.

Comparative Examples 7-3 to 7-8

Except for, as antiaging agents, further adding N,N'-di-2-naphthyl-p-phenylenediamine 1.00 part (made by Ouchi Shinko Chemical Industrial, Nocrac White) (Comparative Example 7-3), 2,2'-methylene bis(4-methyl-6-t-butylphenol) 1.00 part (made by Ouchi Shinko Chemical Industrial, Nocrac NS-6) (Comparative Example 7-4), 2,6-di-t-butyl-4-methylphenol 1.00 part (made by Ouchi Shinko Chemical Industrial, Nocrac 200) (Comparative Example 7-5), 2-mercaptobenzimidazole 1.00 part (made by Ouchi Shinko Chemical Industrial, Nocrac MB) (Comparative Example 7-6), tris(nonylphenyl)phosphite 1.00 part (made by Ouchi Shinko Chemical Industrial, Nocrac TNP) (Comparative Example 7-7), tris(nonylphenyl) phosphite 1.00 part (made by Ouchi Shinko Chemical Industrial, Nocrac TNP), and 2-mercaptobenzimidazole 0.50 part (made by Ouchi Shinko Chemical Industrial, Nocrac MB) (Comparative Example 7-8), the same procedures were performed as in Comparative Example 7-2 to obtain acrylic rubber compositions and similarly evaluate them. The results are shown in Table 14.

TABLE 14

| Formulation | | | Comp. Ex. 7-2 | Comp. Ex. 7-3 | Comp. Ex. 7-4 | Comp. Ex. 7-5 |
|---|---|---|---|---|---|---|
| Carboxyl group-containing acrylic rubber B | Parts by weight | | 100 | 100 | 100 | 100 |
| Carbon black | Parts by weight | | 60 | 60 | 60 | 60 |
| Stearic acid | Parts by weight | | 2 | 2 | 2 | 2 |
| Antiaging agent | Type | | 4,4'-bis(α,α-dimethylbenzyl)diphenylamine | | | |
| | Amount of addition to rubber 100 parts by weight | Parts by weight | 2.00 | | | |
| | Type | | — | N,N'-di-2-naphthyl-p-phenylenediamine | 2,2'-methylene-bis(4-methyl-6-t-butylphenol) | 2,6-di-t-butyl-4-methylphenol |
| | Amount of addition to rubber 100 parts by weight | Parts by weight | — | 1.00 | 1.00 | 1.00 |
| | Type | | — | — | — | — |
| | Amount of addition to rubber 100 parts by weight | Parts by weight | — | — | — | — |
| Hexamethylenediamine carbamate | Parts by weight | | 0.6 | 0.6 | 0.6 | 0.6 |
| 1,3-di-o-tolylguanidine | Parts by weight | | 2 | 2 | 2 | 2 |
| Original properties | Tensile strength [MPa] | | 10.2 | 9.5 | 9.7 | 9.6 |
| | Elongation [%] | | 220 | 220 | 210 | 220 |
| | 100% modulus [MPa] | | 2.8 | 4.5 | 4.6 | 4.2 |
| | Hardness [Duro A] | | 65 | 67 | 69 | 68 |
| Heat resistance test | Rate of change of elongation [%] After 190° C. 500 hours | | −73 | −68 | −71 | −68 |

| Formulation | | | Comp. Ex. 7-6 | Comp. Ex. 7-7 | Comp. Ex. 7-8 |
|---|---|---|---|---|---|
| Carboxyl group-containing acrylic rubber B | Parts by weight | | 100 | 100 | 100 |
| Carbon black | Parts by weight | | 60 | 60 | 60 |
| Stearic acid | Parts by weight | | 2 | 2 | 2 |
| Antiaging agent | Type | | 4,4'-bis(α,α-dimethylbenzyl)diphenylamine | | |
| | Amount of addition to rubber 100 parts by weight | Parts by weight | 2.00 | | |
| | Type | | 2-mercapto-benzimidazole | Tris(nonylphenyl) phosphite | |
| | Amount of addition to rubber 100 parts by weight | Parts by weight | 1.00 | 1.00 | |
| | Type | | — | — | 2-mercapto-benz-imidazole |
| | Amount of addition to rubber 100 parts by weight | Parts by weight | — | — | 0.50 |
| Hexamethylenediamine carbamate | Parts by weight | | 0.6 | 0.6 | 0.6 |
| 1,3-di-o-tolylguanidine | Parts by weight | | 2 | 2 | 2 |
| Original properties | Tensile strength [MPa] | | 8.8 | 9.0 | 8.7 |
| | Elongation [%] | | 210 | 240 | 250 |
| | 100% modulus [MPa] | | 4.1 | 3.7 | 3.7 |
| | Hardness [Duro A] | | 69 | 68 | 70 |
| Heat resistance test | Rate of change of elongation [%] After 190° C. 500 hours | | −71 | −71 | −72 |

Evaluation of Examples 7-4 to 7-11 and Comparative Examples 7-2 to 7-8

As shown in Table 13 and Table 14, in Examples 7-4 to 7-11 which jointly used antiaging agents constituted by the predetermined compound 1 of the present invention and other antiaging agent, even after going through severe conditions of an environment of 190° C. for 500 hours, compared with Comparative Examples 7-2 to 7-8, the rates of change of elongation were close to 0 and the changes in elongation were small. Accordingly, it was confirmed that the cross-linked rubber products obtained by using the acrylic rubber compositions of the present invention were improved in heat resistance regardless of the types of the cross-linking agents and cross-linking accelerators. Further, when jointly using antiaging agents constituted by the predetermined compound 1 of the present invention and other antiaging agent, it was confirmed that, compared with the case of jointly using conventional antiaging agents, the heat resistance is improved.

Methods of Evaluation of Examples 8-1, 8-2 and Comparative Examples 8-1 to 8-3

The various tests of the physical properties in Examples 8-1, 8-2 and Comparative Examples 8-1 to 8-3 were performed by the following methods.
(Test of Original Properties)
The same procedures were performed as in Examples 1-1 to 1-8 and Comparative Examples 1-1 to 1-4 to obtain test pieces and measure the tensile strength (strength), elongation at break (elongation), and hardness.
(Oil Resistance Test)
In accordance with the immersion test method of JIS K6258, the prepared test piece was immersed in commercially available engine oil (made by Castrol, XLD-Diesel CE10W-30) at 150° C. for 168 hours, then the rate of change of volume, tensile strength (strength), elongation at break (elongation), and hardness were measured.
(Heat Resistance Test after Immersion in Engine Oil)
The heat resistance test after immersion in engine oil was performed in accordance with the immersion test method of JIS K6258. The prepared test piece was immersed in commercially available engine oil (made by Castrol, XLD-Diesel CE10W-30) at 150° C. for 168 hours, then pulled up, air dried for 24 hours within a draft at room temperature, then further heated in a 190° C. environment for 168 hours to cause heat degradation and the result was used. Specifically, first, in accordance with JIS K6251, the elongations before and after heating were measured and the following formula was followed to calculate the rate of change and thereby measure the rate of change of elongation. The closer the rate of change of elongation to zero, the higher the heat resistance is judged and the more preferable the result.

Rate of change of elongation (%)=100×[(elongation after heating (%))−(elongation before heating (%))]/(elongation before heating (%))

(Content of Amount of Antiaging Agent in Test Piece)
A test piece before immersion in engine oil was diced, then treated at 90° C. for 8 hours for Soxhlet extraction using chloroform as the solvent to thereby obtain an extract. The extract was dried in vacuo at 40° C. for 2 hours, then tetrahydrofuran 5 ml was added to make the extract dissolve. 1 ml of this solution was taken in a 10 ml measuring flask, then tetrahydrofuran was used to dilute this to 10 ml to obtain a test solution. The prepared test solution was measured by high performance liquid chromatography to quantify the amount of the antiaging agent by using calibration curve method.

In the test piece after the above-mentioned immersion in engine oil as well, in the same way, the amount of antiaging agent in the test piece is assayed, then the following formula is used to find the residual rate of the antiaging agent. The higher the residual rate, the smaller the amount of extraction of the antiaging agent to the oil and the more preferable the result.

Residual rate (%)=100×(amount of antiaging agent after immersion)/(amount of antiaging agent before immersion)

Example 8-1

The same procedure was followed as in Example 2-3 to prepare an acrylic rubber composition. The obtained acrylic rubber composition was used in accordance with the above methods to perform a test on the original properties, oil resistance test, heat resistance test after immersion in engine oil, and measurement of the content of the amount of antiaging agent in the test piece. The results are shown in Table 15.

Example 8-2

Except for changing the amount of the compound 1 (antiaging agent) to 2.00 parts, the same procedure was followed as in Example 8-1 to obtain an acrylic rubber composition and similarly evaluate it. The results are shown in Table 15.

Comparative Example 8-1

Except for not adding the compound 1 (antiaging agent), the same procedure was followed as in Example 8-1 to obtain an acrylic rubber composition and similarly evaluate it. The results are shown in Table 15.

Comparative Examples 8-2, 8-3

Except for using, instead of the compound 1 (antiaging agent), 4,4'-bis(α,α-dimethylbenzyl)diphenylamine (antiaging agent, made by Chemtura, Nauguard 445) and making the amounts 1.00 part (Comparative Example 8-2) and 2.00 parts (Comparative Example 8-3), the same procedures were followed as in Example 8-1 to obtain acrylic rubber compositions and similarly evaluate them. The results are shown in Table 15.

TABLE 15

| | Formulation | Ex. 8-1 | Ex. 8-2 | Comp. Ex. 8-1 | Comp. Ex. 8-2 | Comp. Ex. 8-3 |
| --- | --- | --- | --- | --- | --- | --- |
| Carboxyl group-containing acrylic rubber A | Parts by weight | 100 | 100 | 100 | 100 | 100 |
| Carbon black | Parts by weight | 60 | 60 | 60 | 60 | 60 |
| Stearic acid | Parts by weight | 2 | 2 | 2 | 2 | 2 |
| Antiaging agent | Type | Compound 1 | Compound 1 | — | 4,4'-bis(α,α-dimethylbenzyl)diphenylamine | 4,4'-bis(α,α-dimethylbenzyl)diphenylamine |

TABLE 15-continued

| Formulation | | Ex. 8-1 | Ex. 8-2 | Comp. Ex. 8-1 | Comp. Ex. 8-2 | Comp. Ex. 8-3 |
|---|---|---|---|---|---|---|
| Amount of addition to rubber 100 parts by weight | Parts by weight | 1.00 | 2.00 | — | 1.00 | 2.00 |
| 2,2-bis[4-(4-aminophenoxy)phenyl] propane | Parts by weight | 1 | 1 | 1 | 1 | 1 |
| Dialkyl($C_8$ to $C_{18}$)amine | Parts by weight | 2 | 2 | 2 | 2 | 2 |
| Original properties | Tensile strength [MPa] | 9.8 | 9.8 | 10.1 | 10.2 | 10.1 |
| | Elongation [%] | 260 | 250 | 250 | 250 | 260 |
| | Hardness [Duro A] | 64 | 63 | 63 | 63 | 64 |
| Oil resistance test After 150° C. 168 hours | Rate of change of volume [%] | +5 | +5 | +6 | +5 | +5 |
| | Tensile strength [MPa] | 10.0 | 9.7 | 9.7 | 9.8 | 9.5 |
| | Elongation [%] | 220 | 220 | 210 | 220 | 220 |
| | Hardness [Duro A] | 68 | 67 | 69 | 68 | 67 |
| Heat resistance test after immersion in engine oil | Rate of remainder of antiaging agent [%] After 150° C. 168 hours | 45.0 | 45.0 | — | 6.8 | 7.0 |
| | Rate of change of elongation [%] After 190° C. 168 hours | −35 | −40 | −51 | −50 | −48 |

Evaluation of Examples 8-1, 8-2 and Comparative Examples 8-1 to 8-3

As shown in Table 15, in Examples 8-1 and 8-2 which used antiaging agents constituted by predetermined compound 1 of the present invention, the original properties after the oil resistance test were excellent. Further, even after immersion in engine oil, the antiaging agent constituted by the compound 1 remained in a large amount in the cross-linked rubber products, the rates of change of elongation were small, and the heat resistances were excellent. On the other hand, in Comparative Examples 8-1 to 8-3, after immersion in engine oil, the rates of change of elongation were large and the heat resistances were inferior. In particular, in Comparative Examples 8-2 and 8-3, in the cross-linked rubber products, the residual amounts of the antiaging agents constituted by 4,4'-bis(α,α-dimethylbenzyl)diphenylamine became small.

The invention claimed is:

1. An acrylic rubber composition which contains, with respect to 100 parts by weight of acrylic rubber, a compound which is expressed by the following general formula (1) in 0.1 to 50 parts by weight and a cross-linking agent in 0.05 to 20 parts by weight,

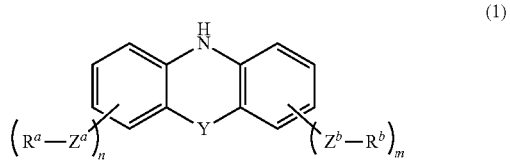

(1)

wherein, in said general formula (1), Y indicates a chemical single bond or —$SO_2$—, $R^a$ and $R^b$ respectively independently indicate substitutable $C_1$ to $C_{30}$ organic groups, $Z^a$ and $Z^b$ respectively independently indicate chemical single bonds or —$SO_2$—, n and m respectively independently are 0 or 1, at least one of n and m being 1.

2. The acrylic rubber composition as set forth in claim 1, wherein, in the compound which is expressed by said general formula (1), $R^a$ and $R^b$ respectively independently are substitutable linear or branched $C_2$ to $C_8$ alkyl groups or substitutable phenyl groups.

3. The acrylic rubber composition as set forth in claim 1, wherein, in the compound which is expressed by said general formula (1), Y is —$SO_2$—, $R^a$ and $R^b$ respectively independently are substitutable linear or branched $C_2$ to $C_8$ alkyl groups, $Z^a$ and $Z^b$ are chemical single bonds, and n and m are 1.

4. The acrylic rubber composition as set forth in claim 1, wherein the content, with respect to 100 parts by weight of said acrylic rubber, of the compound which is expressed by said general formula (1) is 0.3 to 5 parts by weight.

5. The acrylic rubber composition as set forth in claim 1, wherein said acrylic rubber is a carboxyl group-containing acrylic rubber.

6. The acrylic rubber composition as set forth in claim 1, wherein said acrylic rubber is an epoxy group-containing acrylic rubber.

7. The acrylic rubber composition as set forth in claim 1, wherein said acrylic rubber is a halogen atom-containing acrylic rubber.

8. The acrylic rubber composition as set forth in claim 1, wherein said acrylic rubber is a carboxyl group- and halogen atom-containing acrylic rubber.

9. The acrylic rubber composition as set forth in claim 1, wherein said acrylic rubber contains ethylene-acrylate rubber in 0.1 to 100 wt %.

10. The acrylic rubber composition as set forth in claim 1, wherein the acrylic rubber composition further contains at least one type of other antiaging agent other than the compound which is expressed by said general formula (1), and the content, with respect to 100 parts by weight of the acrylic rubber, of the total of the compound which is expressed by said general formula (1) and said other antiaging agent is 0.1 to 50 parts by weight.

11. A cross-linked rubber product obtained by cross-linking the acrylic rubber composition as set forth in claim 1.

12. The cross-linked rubber product as set forth in claim 11, which is an extruded product.

13. The cross-linked rubber product as set forth in claim 11, which is a seal member.

* * * * *